United States Patent
Baura

(10) Patent No.: US 6,514,211 B1
(45) Date of Patent: Feb. 4, 2003

(54) METHOD AND APPARATUS FOR THE NONINVASIVE DETERMINATION OF ARTERIAL BLOOD PRESSURE

(75) Inventor: Gail D. Baura, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 0 days.

(21) Appl. No.: 09/489,160

(22) Filed: Jan. 21, 2000

Related U.S. Application Data

(63) Continuation-in-part of application No. 09/342,549, filed on Jun. 29, 1999.

(51) Int. Cl.⁷ .................................................. A61B 5/00
(52) U.S. Cl. ........................ 600/490; 600/500; 600/485
(58) Field of Search ................................ 600/485, 490, 600/493–6, 500

(56) References Cited

U.S. PATENT DOCUMENTS

| | | |
|---|---|---|
| 3,527,197 A | 9/1970 | Ware et al. |
| 3,601,120 A | 8/1971 | Massie et al. |
| 3,617,993 A | 11/1971 | Massie et al. |
| 3,663,932 A | 5/1972 | Mount et al. |
| 3,791,378 A | 2/1974 | Hochbert et al. |
| 3,885,551 A | 5/1975 | Massie |
| 4,109,647 A | 8/1978 | Stern et al. |
| 4,127,114 A | 11/1978 | Bretscher |
| 4,154,231 A | 5/1979 | Russell |
| 4,239,047 A | 12/1980 | Griggs, III et al. |

(List continued on next page.)

FOREIGN PATENT DOCUMENTS

| | | |
|---|---|---|
| DE | 42 18 319 A1 | 12/1993 |
| EP | 284 095 B1 | 3/1988 |
| EP | 342 249 A1 | 5/1988 |
| EP | 0 299 827 | 1/1989 |
| EP | 0595 666 B1 | 9/1993 |

(List continued on next page.)

OTHER PUBLICATIONS

Hartley, C.J., et al., "An Ultrasonic Method for Measuring Tissue Displacement: Technical Details and Validation for Measuring Myocardial Thickening," IEEE Trans Biomed, (1991) 38:735–747.

Anderson, E.A., et al. (1989) Flow–mediated and reflex changes in large peripheral artery tone in humans. Circulation 79:93–100.

(List continued on next page.)

*Primary Examiner*—Robert L. Nasser
(74) *Attorney, Agent, or Firm*—Gazdzinski & Associates

(57) ABSTRACT

A method and apparatus for determining the mean arterial blood pressure (MAP) of a subject during tonometric conditions. In one embodiment, the apparatus comprises one or more pressure and ultrasound transducers placed over the radial artery of a human subject's wrist, the latter transmitting and receiving acoustic energy so as to permit the measurement of blood velocity during periods of variable compression of the artery. During compression, the ultrasound velocity waveforms are recorded and processed using time-frequency analysis. The time at which the mean time-frequency distribution is maximal corresponds to the time at which the transmural pressure equals zero, and the mean pressure read by the transducer equals the mean pressure within the artery. In another aspect of the invention, the ultrasound transducer is used to position the transducer over the artery such that the accuracy of the measurement is maximized. In yet another aspect of the invention, a wrist brace useful for measuring blood pressure using the aforementioned apparatus is disclosed. A method of continuously estimating systolic and diastolic pressure is also described.

15 Claims, 26 Drawing Sheets

U.S. PATENT DOCUMENTS

| | | | |
|---|---|---|---|
| 4,249,540 A | | 2/1981 | Koyama et al. |
| 4,349,034 A | | 9/1982 | Ramsey, III |
| 4,476,875 A | | 10/1984 | Nilsson et al. |
| 4,566,462 A | | 1/1986 | Janssen |
| 4,590,948 A | | 5/1986 | Nilsson |
| 4,596,254 A | | 6/1986 | Adrian et al. |
| 4,719,923 A | | 1/1988 | Hartwell et al. |
| 4,754,761 A | | 7/1988 | Ramsey, III et al. |
| 4,880,013 A | | 11/1989 | Chio |
| 5,030,956 A | | 7/1991 | Murphy |
| 5,072,733 A | | 12/1991 | Spector et al. |
| 5,094,244 A | | 3/1992 | Callahan et al. |
| 5,158,091 A | | 10/1992 | Butterfield et al. |
| 5,163,438 A | | 11/1992 | Gordon et al. |
| 5,238,000 A | | 8/1993 | Niwa |
| 5,273,046 A | | 12/1993 | Butterfield et al. |
| 5,368,039 A | | 11/1994 | Moses |
| 5,406,952 A | * | 4/1995 | Barnes et al. ............... 600/500 |
| 5,479,928 A | | 1/1996 | Cathignol et al. |
| 5,533,511 A | * | 7/1996 | Kaspari et al. ............. 600/500 |
| 5,590,649 A | | 1/1997 | Caro et al. |
| 5,833,618 A | | 11/1998 | Caro et al. |
| 5,848,970 A | | 12/1998 | Voss et al. |
| 5,882,311 A | * | 3/1999 | O'Rourke ................... 600/500 |
| 5,895,359 A | | 4/1999 | Peel, III |
| 5,916,180 A | | 6/1999 | Cundari et al. |
| 5,964,711 A | | 10/1999 | Voss et al. |
| 6,010,457 A | * | 1/2000 | O'Rourke ................... 600/500 |
| 6,176,831 B1 | | 1/2001 | Voss et al. |
| 6,228,034 B1 | | 5/2001 | Voss et al. |
| 6,270,461 B1 | | 8/2001 | Chio |
| 6,340,349 B1 | * | 1/2002 | Archibald et al. .......... 600/494 |

FOREIGN PATENT DOCUMENTS

| | | |
|---|---|---|
| EP | 0 603 666 A3 | 12/1993 |
| EP | 0818176 A | 1/1998 |
| WO | WO 92/07508 | 10/1991 |
| WO | WO 95/00074 | 1/1995 |
| WO | WO 98/25511 A | 6/1998 |
| WO | WO 00/03635 | 1/2000 |

OTHER PUBLICATIONS

Boashash, B., et al. (1987) An efficient real–time implementation of the Wigner–Ville distribution. IEEE Trans ASSP 35:1611–1618.

Drzewiecki, G.M., et al. (1985) Generalization of the transmural pressure–area relation for the remoral artery. $7^{th}$ Annual IEEE EMBS Conference 507,510.

Hoeks, A.P.G., et al. (1985) Transcutaneous detection of relative changes in artery diameter. Ultrasound in Med and Bio 11:51–59.

Drzewiecki, G. (1995) "Noninvasive Assessment of Arterial Blood Pressure and Mechanics", The Biomedical Engineering Handbook CRC Press, Boca Raton, FL, pp. 1196–1211.

Carson, E. R. et al. (1983) "The Mathematical Modeling of Metabolic and Endocrine Systems: Model Formulation, Identification, and Validation", John Wiley & Sons, NY, pp. 185–189.

Cariou, Alain, et al. (1998) "Noninvasive Cardiac Output Monitoring by Aortic Blood Flow Determination: Evaluation of the Sometec Cynemo–3000 System," Critical Care Medicine, vol. 26, No. 12, pp. 2066–2072.

Advertisement for HemoSonic™ 100 by Arrow International—licensed under U.S. Pat. No. 5,479,928 listed above.

Mehra, Mandeep R., et al. (May/Jun. 2000) "Emergence of Electronic Home Monitoring In Chronic Heart Failure: Rationale, Feasibility, and Early Results with the HomMed Sentry–Observer System," (consisting of 3 pages).

* cited by examiner

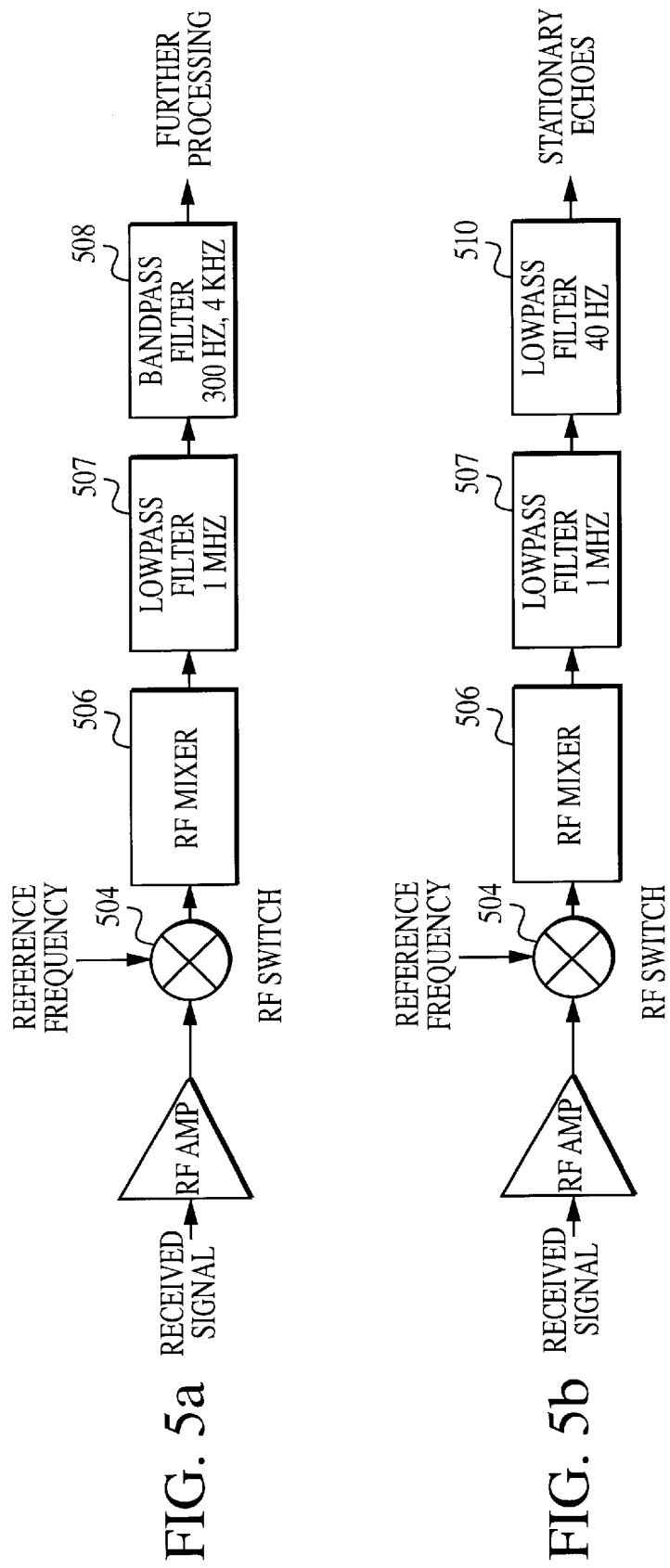

(PART 1 OF 3)

(PART 2 OF 3)

(PART 3 OF 3)

METHOD AND APPARATUS FOR THE NONINVASIVE DETERMINATION OF ARTERIAL BLOOD PRESSURE

This application is a continuation-in-part of U.S. patent application Ser. No. 09/342,549 entitled "Method And Apparatus For The Noninvasive Determination Of Arterial Blood Pressure" filed Jun. 29, 1999, and assigned to the Applicant herein.

BACKGROUND OF THE INVENTION

1. Field of the Invention

This invention relates generally to methods and apparatus for monitoring the blood pressure of a living subject, and specifically to the non-invasive monitoring of arterial blood pressure using acoustic techniques.

2. Description of the Related Art

Three well known techniques have been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above generally have been effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. This theory is illustrated graphically in FIG. 1. Note that in FIG. 1, bone or another rigid member is assumed to lie under the artery.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Prior art tonometry systems are also quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery.

Perhaps the most significant drawback to arterial tonometry systems in general is their inability to continuously monitor and adjust the level of arterial wall compression to an optimum level of zero transmural pressure. Generally, optimization of arterial wall compression has been achieved only by periodic recalibration. This has required an interruption of the subject monitoring function, which sometimes can occur during critical periods. This disability severely limits acceptance of tonometers in the clinical environment.

It is also noted that the maximum pulsatile theory described above has only been demonstrated to date in excised canine arteries, and not in vivo. See, for example, Drzewiecki, G. M, et al, "Generalization of the transmural pressure-area relation for the femoral artery", $7^{th}$ Annual IEEE EMBS Conference, 1985, pp.507–510. Accordingly, the maximum peak-to-peak amplitude in vivo may not occur at the arterial pressure at which the transmural pressure equals zero. In fact, during anecdotal studies performed by the applicant herein using two prior art tonometry systems (with which several hundred applanation sweeps were recorded under numerous test conditions), the maximum pulsatile theory described above never yielded measured mean arterial pressure (MAP) that was consistently similar to the average of two cuff pressure measurements taken immediately before and after the sweep. These factors suggest that prior art maximum pulsatile theory devices may produce significant errors in measured MAP.

Yet another disability with prior art tonometry systems is the inability to achieve imprecise placement of the tonometric sensors over the artery being measured. Similarly, even if properly placed at the outset of a measurement, the movement of the subject during the measurement process may require that the sensors be repositioned periodically with respect to the artery, a capability that prior art tonometric systems do not possess. Proper sensor placement helps assure that representative data is obtained from the subject during measurement, and that accurate results are obtained.

Based on the foregoing, there is a clear need for an apparatus, and related method, for non-invasively and continually monitoring a subject's arterial blood pressure, with reduced susceptibility to noise and subject movement, and relative insensitivity to placement of the apparatus on the subject. Such an improved apparatus and method would also obviate the need for frequent recalibration of the system while in use on the subject. Furthermore, it would be desirable to make certain components of the apparatus in contact with the subject disposable, thereby allowing for the cost effective replacement of these components at regular intervals.

SUMMARY OF THE INVENTION

The invention disclosed herein addresses the foregoing needs by providing an improved apparatus and method for non-invasively monitoring the arterial blood pressure of a subject.

In a first aspect of the invention, a method of continuously and non-invasively estimating the blood pressure existing within the blood vessel of a subject is disclosed. The method generally comprises: estimating a first pressure within the vessel; estimating a second pressure within the vessel; sensing a pressure waveform from the vessel; modeling a mechanical impulse response of the vessel as a mathematical function based at least in part on the estimated first and second pressures to derive a scaling factor; and using the scaling factor, the sensed pressure waveform, and the second pressure to estimate continuously the blood pressure within the vessel. In one exemplary embodiment, the act of estimating pressure comprises: transmitting an acoustic signal into and receiving an echo from the vessel; analyzing the echo to estimate the velocity of blood flowing in the vessel; forming a time-frequency representation of velocity; and generating an estimate of the second pressure when the time-frequency representation satisfies a given condition. In another exemplary embodiment, the act of modeling as a mathematical function comprises (i) modeling as a linear autogression function and (ii) selecting the order of the autogression function based at least in part on standard deviation and residuals.

In a second aspect of the invention, improved apparatus for continuously and non-invasively estimating the blood pressure existing within the blood vessel of a subject is disclosed. The apparatus generally comprises: a sensor adapted to detect a pressure waveform from the vessel and generate electrical signals relating thereto; a processor operatively coupled to the sensor and adapted to process the electrical signals, the processing comprising at least: (i) estimating a first pressure within the vessel; (ii) estimating a second pressure within the vessel; (iii) deriving a scaling factor by modeling a mechanical impulse response of the vessel as a function based at least in part on the estimated first and second pressures; and (iv) continuously estimating the blood pressure within the vessel based on the scaling factor, the pressure waveform, and at least one of the first and second pressures. In one exemplary embodiment, the apparatus includes both a tonometric pressure transducer and an ultrasonic transducer which, in conjunction with supporting signal processing circuitry, measure both the arterial applanation and arterial blood velocity, respectively from the radial artery of a human being. The transducers and their aassociated processing circuitry track the blood velocity in the radial artery during applanation sweeps; i.e., the time period beginning when the artery is overcompressed, and ending when the artery is undercompressed, by emitting acoustic pulses and measuring the Doppler shift in the returns or reflections of the acoustic energy from cells present in the blood. The time- frequency distribution is determined from the velocity data, as calculated by an algorithm running on a digital signal processor (DSP). The time at which the time- frequency distribution is maximized corresponds to the time at which the transmural pressure approximately equals zero, and the mean pressure read by the pressure transducer equals the MAP. The measurements of applanation and blood velocity using the apparatus are largely unaffected by the orientation of the transducers on the subject's wrist.

These and other features of the invention will become apparent from the following description of the invention, taken in conjunction with the accompanying drawings.

BRIEF DESCRIPTION OF THE DRAWINGS

FIG. 3b is a block diagram illustrating a first embodiment of the method of estimating the time-frequency distribution used in conjunction with the method of FIG. 3a.

FIGS. 5a–5b are functional block diagrams of two embodiments of ultrasound filter circuits useful for measurement of Doppler shift frequencies and stationary echoes.

DETAILED DESCRIPTION OF THE INVENTION

Reference is now made to the drawings wherein like numerals refer to like parts throughout.

It is noted that while the invention is described herein in terms of a method and apparatus for monitoring arterial blood pressure suitable for use on the radial artery (i.e., wrist) of a human subject, the invention may also conceivably be embodied or adapted to monitor arterial blood pressure at other locations on the human body, as well as monitoring blood pressure on other warm-blooded species. All such adaptations and alternate embodiments are considered to fall within the scope of the claims appended hereto.

Figure 1:
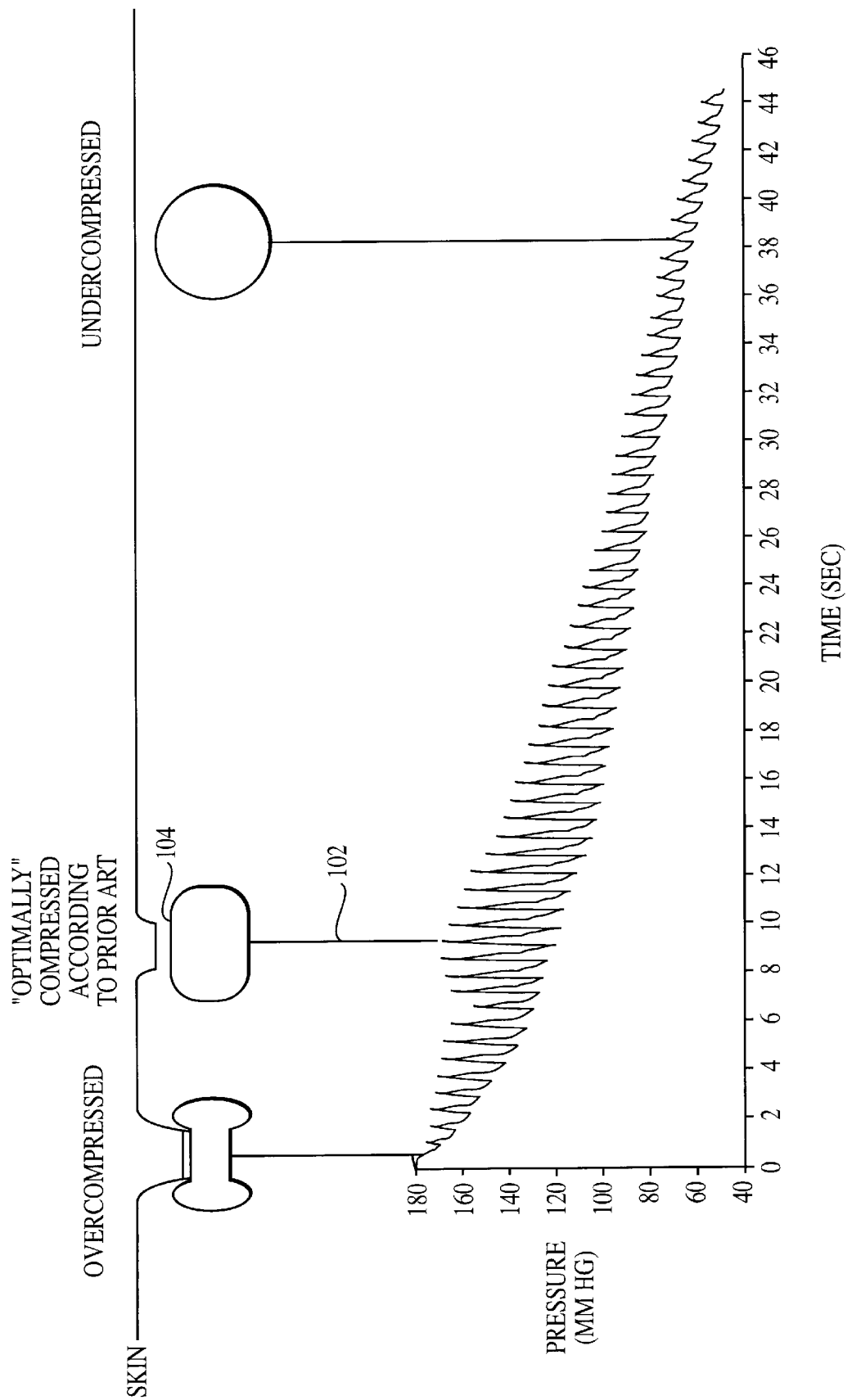
FIG. 1 is a composite graph illustrating the cross-sectional shape of an artery as a function of applied pressure and time, as correlated to blood pressure waveforms, according to prior art arterial tonometry theory.
Figure 2:
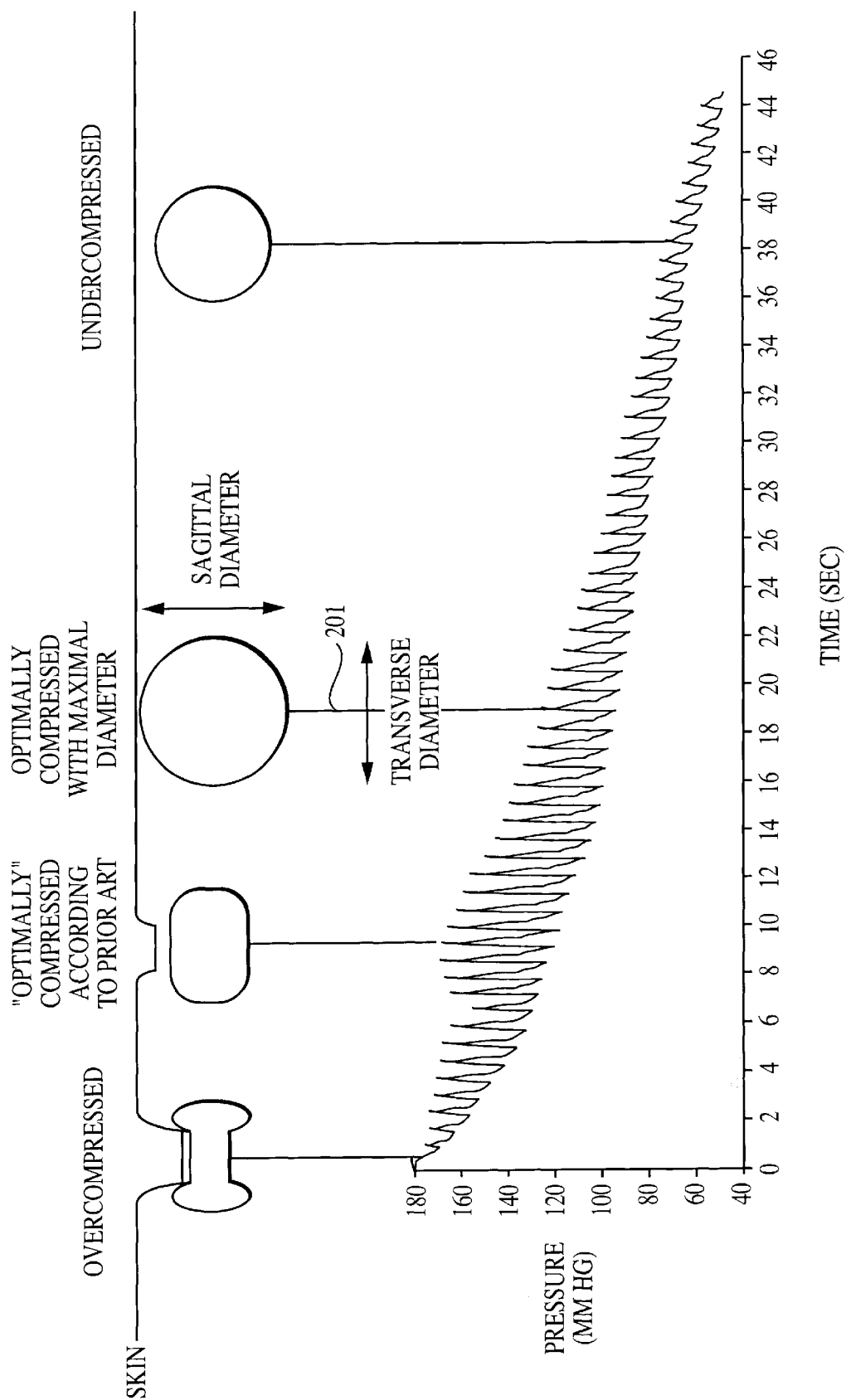
FIG. 2 is a composite graph illustrating the cross-sectional shape of an artery as a function of applied pressure and time, illustrating the hypothesized mechanism behind the maximum time-frequency distribution applanation concept of the present invention.

Referring now to FIGS. 1 and 2, the hypothesized maximum arterial diameter applanation concept of the present invention is described. Under the prior art tonometry theory previously described with respect to FIG. 1, the maximum pulsatile pressure is assumed to correspond to the state of zero transmural pressure; i.e., the point in time 102 when the arterial pressure is perpendicular to the arterial wall surface 104 and is the only pressure detected by the tonometer pressure transducer (not shown). Hence, prior art tonometry systems utilizing this theory measure the maximum peak-to-peak blood pressure within the artery, and correlate this pressure to a state of zero transmural pressure.

In the invention disclosed herein, however, the optimum applanation is found by evaluating one or more other parameters rather than detecting the maximum pulsatile pressure as in the prior art; i.e., in one embodiment, the invention estimates the maximum time-frequency distribution during an applanation sweep. The maximum time-frequency distribution may be indicative of, inter alia, the maximum arterial diameter. As used herein, the term "diameter" includes the actual diameter of a blood vessel measured in a particular dimension or direction and at a particular point in time, as well as any related parameters calculated based on the actual diameter to include, without limitation, mean diameter calculated over a particular time interval, mean diameter as a function of position on the blood vessel, and maximum diastolic diameter (Appendix A). In the maximum time-frequency method of the present invention, it is hypothesized that the optimum applanation occurs at that point in time 201 during the applanation sweep when the external applied pressure has decreased sufficiently so that internal pressure may oppose it, allowing the sagittal arterial diameter to transiently increase to its maximum as a consequence of reactive hyperemia. This phenomenon may occur at the true mean arterial pressure, during which the transmural pressure equals zero, as shown in FIG. 2.

Method of Measuring Mean Arterial Pressure (MAP)

Figure 3A:
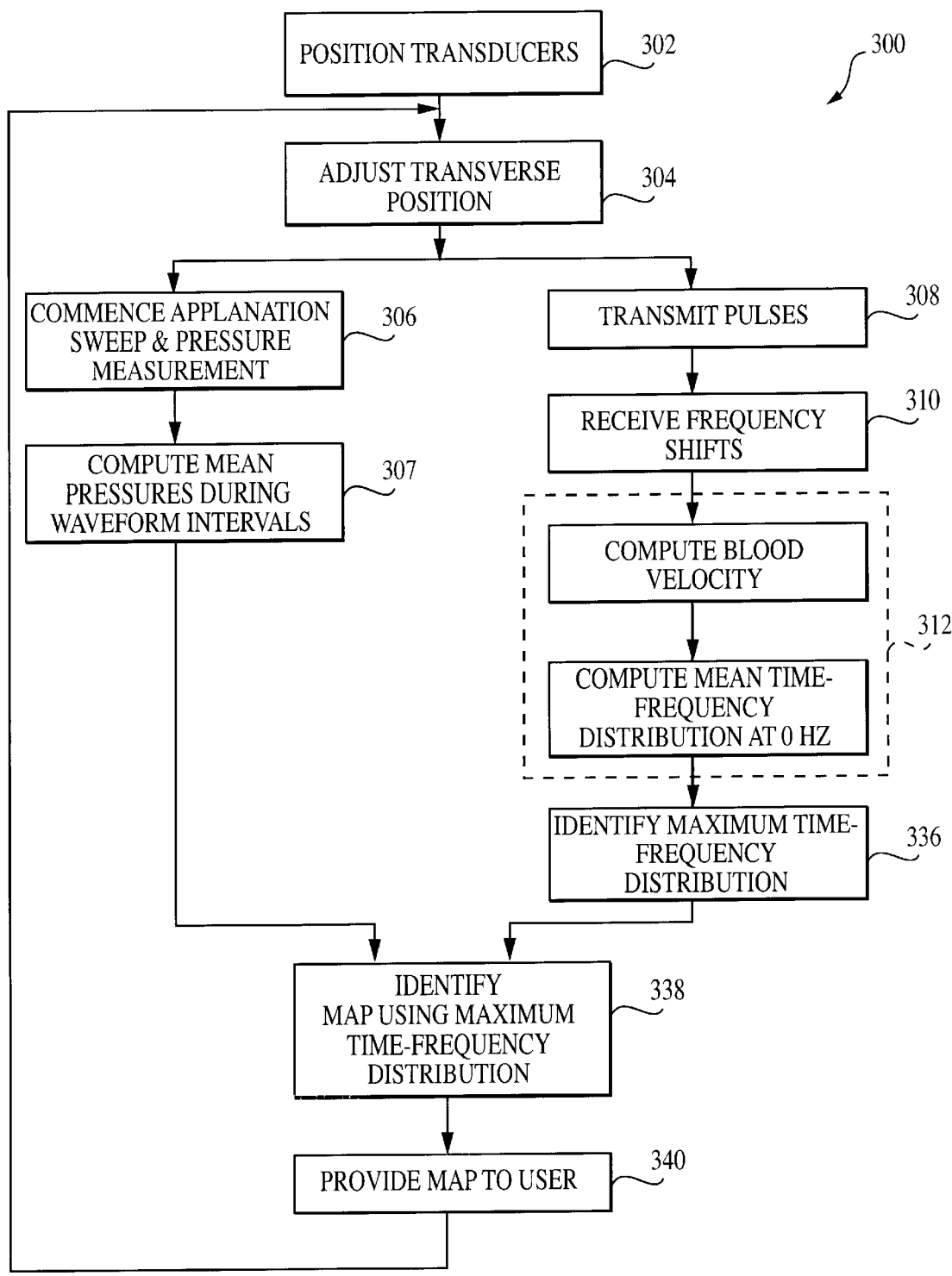
FIG. 3a is a block diagram illustrating one embodiment of the method of measuring arterial blood pressure according to the present invention.

Referring now to FIG. 3a, one embodiment of the maximum time-frequency method of measuring mean arterial pressure according to the present invention is described. In the method 300 of FIG. 3a, pressure and ultrasonic transducers (described in greater detail below with reference to FIGS. 5, 6, and 7) are first positioned generally atop the radial artery of the subject in step 302. As is well known in the medical sciences, the radial artery in the human being runs longitudinally along the inner surface of the wrist and forearm below the surface tissue. Very precise transverse positioning of the ultrasonic and pressure transducers is accomplished in step 304 by generating a series of acoustic pulses, which produce echoes via interaction with tissue and/or red blood cells present in the artery. The amplitude of these echoes is measured as a function of position, and the transverse position of the transducer element is adjusted so that the amplitude is minimized. At the position overlying the center of the artery, the echoes are mostly absorbed by the blood, as compared to absorption by tissue. Exact positioning over the artery increases the signal-to-noise ratio (SNR) and therefore accuracy of the blood pressure measurement.

Next, in step 306, a decreasing applanation sweep of the selected artery is commenced. The applanation sweep begins by overcompressing the artery against the underlying bone (or other rigid member) using the aforementioned pressure transducer such that a cross section similar to that shown in FIG. 2 is obtained. As the sweep progresses, the compression of the artery is gradually reduced until the artery is ultimately not compressed at all. During the progression of the applanation sweep, the pressure within the artery during each heartbeat is measured using the pressure transducer, and the mean value of each pressure waveform computed in step 307. Concurrently with the applanation sweep of step 306, acoustic pulses are generated and transmitted into the artery using the ultrasonic transducer in step 308. These pulses are reflected by various structures or entities within the artery (such as the artery walls, and the red blood cells within the subject's blood), and subsequently received as frequency shifts by the ultrasonic transducer in step 310. Next, in step 312, the blood velocity and time-frequency distribution are calculated using the received frequency shifts. Specifically, the frequencies of those echoes reflected by blood cells within the blood flowing in the artery will differ from that of the transmitted acoustic pulses due to the motion of the blood cells. This well known "Doppler shift" in frequency is used to calculate the blood velocity. Other components of the transmitted pulse are reflected by effectively stationary objects (such as the arterial walls 104); the phase of these echoes is used to calculate the time-frequency distribution. The calculation of the blood velocity and time-frequency distribution are described in greater detail below with respect to FIGS. 3b and 3c. The mean time-frequency distribution at 0 Hz is computed during each heartbeat in step 312. In step 336, the mean time-frequency distribution measurements obtained in step 312 are analyzed to locate the maximum mean time-frequency value occurring during the applanation sweep; the mean arterial pressure corresponding to the maximum time-frequency distribution is then identified in step 338. This mean arterial pressure value is then provided to the user as the MAP in step 340.

Figure 3B:
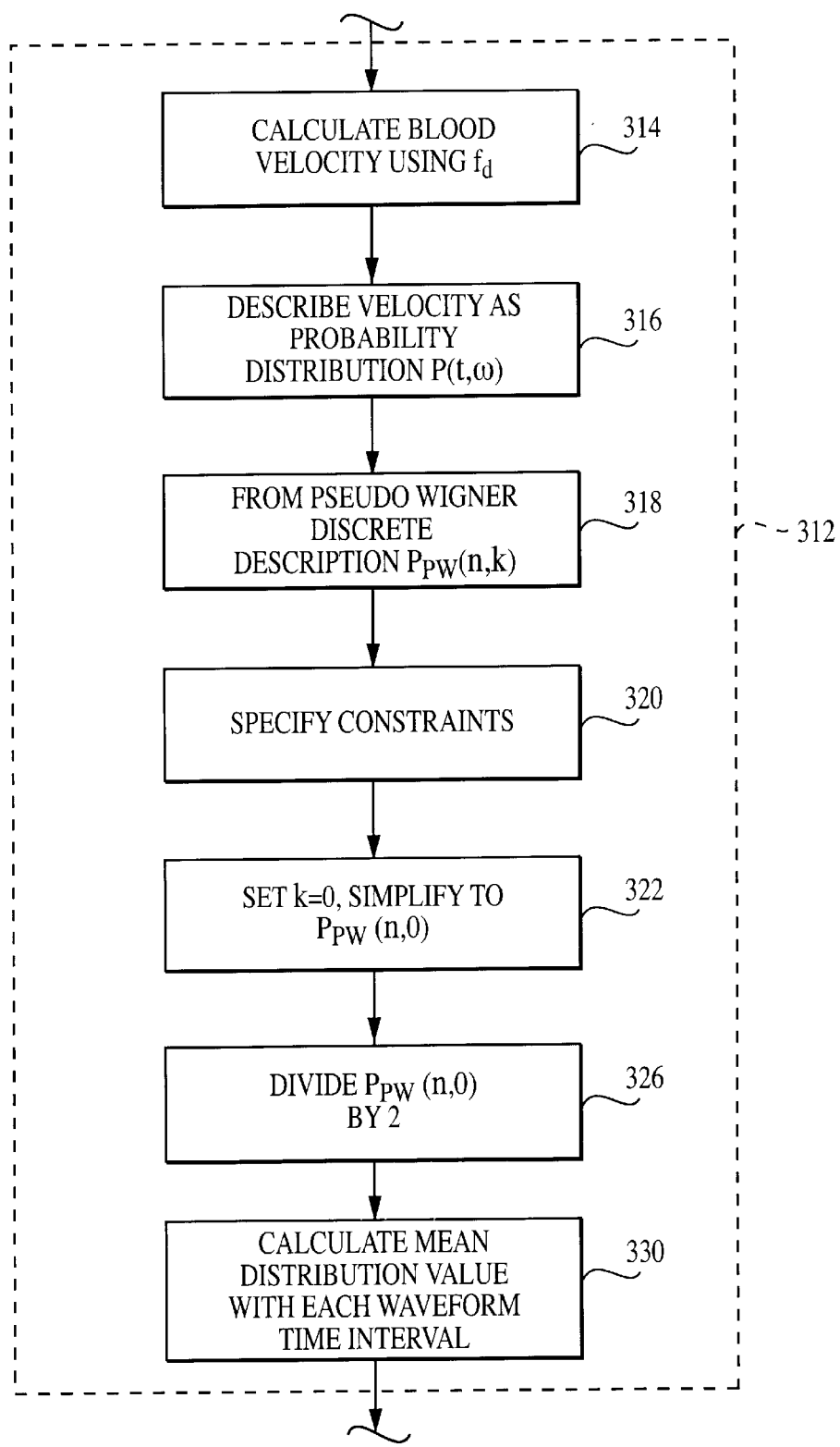

Referring now to FIG. 3b, a first embodiment of the method of determining blood velocity and time-frequency distribution according to the invention is described. As shown in FIG. 3b, the first sub-step 314 of step 312 comprises using the Doppler frequency, $f_d$, and Eqn. 1 to obtain the mean blood velocity, $|\bar{v}|$:

$$|\bar{v}| = \frac{f_d c}{2 f_o \cos\theta}, \quad \text{(Eqn. 1)}$$

where $f_o$ is the transmitted signal frequency, $\theta$ is the transmission angle of the acoustic energy referenced to a vector normal to the longitudinal axis of the artery, and c is the speed of sound in soft tissue.

In the embodiment of FIG. 3b, a time-frequency representation of the type well known in the mathematical arts is calculated for the blood velocity. A time-frequency representation is a two-dimensional mapping of the fraction of the energy of a one-dimensional signal at time, t, and angular frequency, $\omega$. This joint energy density, $P(t, \omega)$, is commonly referred to as a "probability distribution" or "distribution", referring to its historical utility in quantum mechanics. This distribution is described in sub-step 316 of FIG. 3 using the form shown in Eqn. 2:

$$P(t, \omega) = \frac{1}{4\pi^2} \int\int \lambda(\theta, \tau) u^*(\theta - 0.5\tau) u(\theta + 0.5\tau) e^{-j\theta t - j\tau\omega} d\theta d\tau, \quad \text{(Eqn. 2)}$$

where $d\theta$ and $d\tau$ are dummy integration variables, $\lambda(\theta, \tau)$ is a two-dimensional function known as a "kernel", and u(t) is the input signal. The simplest distribution is the Wigner or Wigner-Ville distribution, which uses a kernel of $\lambda(\theta, \tau)=1$. Note that Eqn. 2 uses continuous time, t, while an actual implementation of the distribution requires discrete time, n. Next, using discrete frequency, k, the discrete time description of the Wigner distribution (also known as a Pseudo Wigner distribution) is formed per sub-step 318 of FIG. 3b, as shown in Eqn. 3.

$$P_{PW}(n, k) = 2\sum_{\tau=-L}^{+L} e^{-j4\pi k\tau/N} u^*(n - \tau) u(n + \tau), \quad \text{(Eqn. 3)}$$

where $$k = \frac{\omega}{2\pi},$$

u(t) and its complex conjugate are sample-limited to $\{-K/2, +K/2\}$, K is even, and N=K+1. Next, in sub-step 320, a rectangular window is specified, so that $L=K/2-|n|$. See, e.g., Boashash, B., et al, "An efficient real-time implementation of the Wigner-Ville distribution", *IEEE Trans ASSP*, 35:1611–1618, 1987, which is incorporated herein by reference in its entirety.

In sub-step 322, a frequency of k=0 Hz is selected, and the Pseudo Wigner calculation simplified to the form of Eqn. 4:

$$P_{PW}(n, 0) = 2\sum_{\tau=-L}^{+L} u^*(n - \tau) u(n + \tau). \quad \text{(Eqn. 4)}$$

Eqn. 4 is equivalent to direct integration of the autocorrelation of a signal, scaled by a factor of 2. Autocorrelation is well known in the signal processing arts. In sub-step 326, Eqn. 4 is divided by a factor of 2. Lastly, in sub-step 330, the mean distribution value is calculated for each heartbeat or pressure waveform time interval.

It is noted that various features in the time-frequency distribution calculated using the method 300 of FIG. 3a can be emphasized by specifying a different kernel. For example, using the kernel $\lambda(\theta, \tau) = e^{-\theta^2\tau^2/\sigma}$ where $\sigma$ is a parameter, to calculate the Choi-Williams distribution, the time-frequency fluctuations within each heartbeat would be reduced. Feature analysis at other frequencies is also possible since similar mean distributions are calculated, but at the expense of more complicated computations. This flexibility in feature selection further enhances the utility of the time-frequency distribution in the present embodiment.

Figure 4A:
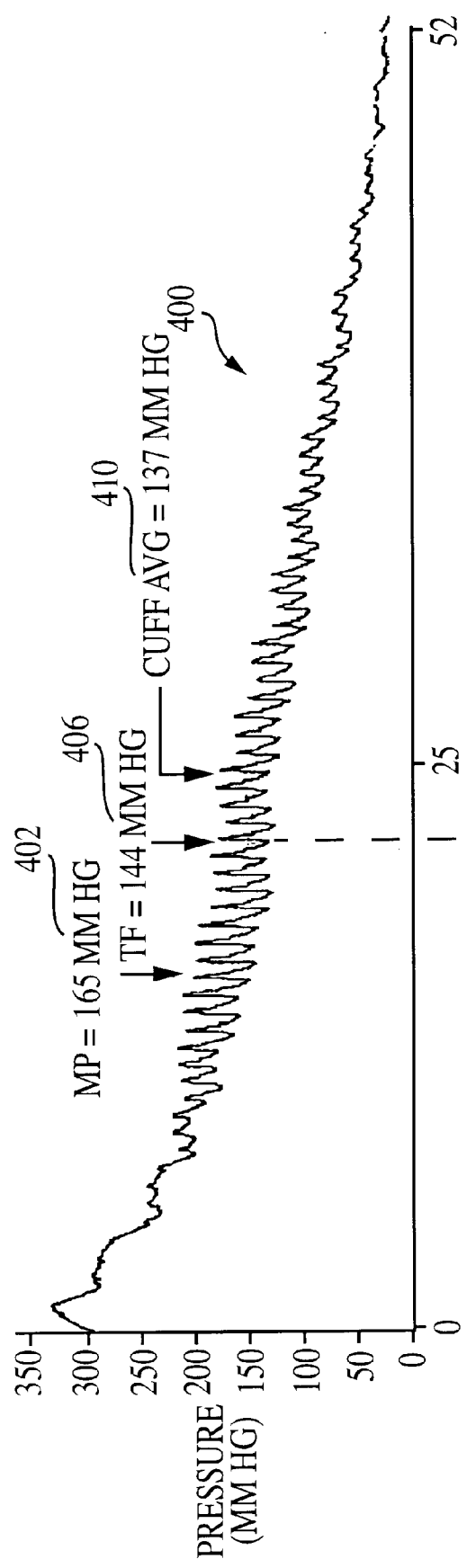
FIGS. 4a–4c are exemplary plots illustrating the relationship between pressure and time, blood velocity and time, and time-frequency distribution and time, respectively, based on typical data obtained using the method of FIGS. 3a–3b.
Figure 4B:
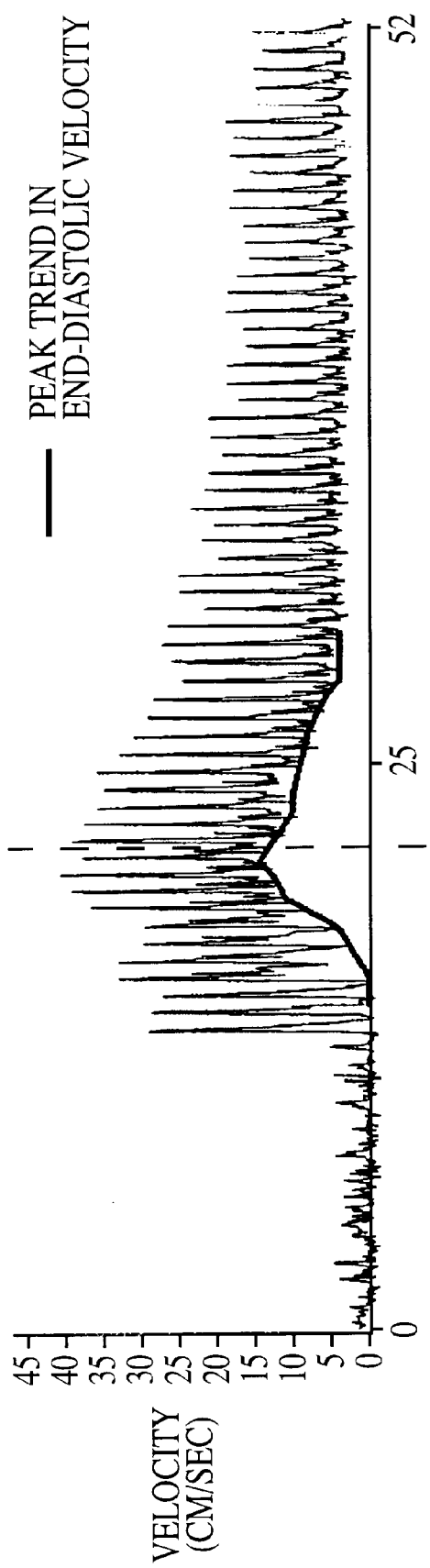
Figure 4C:
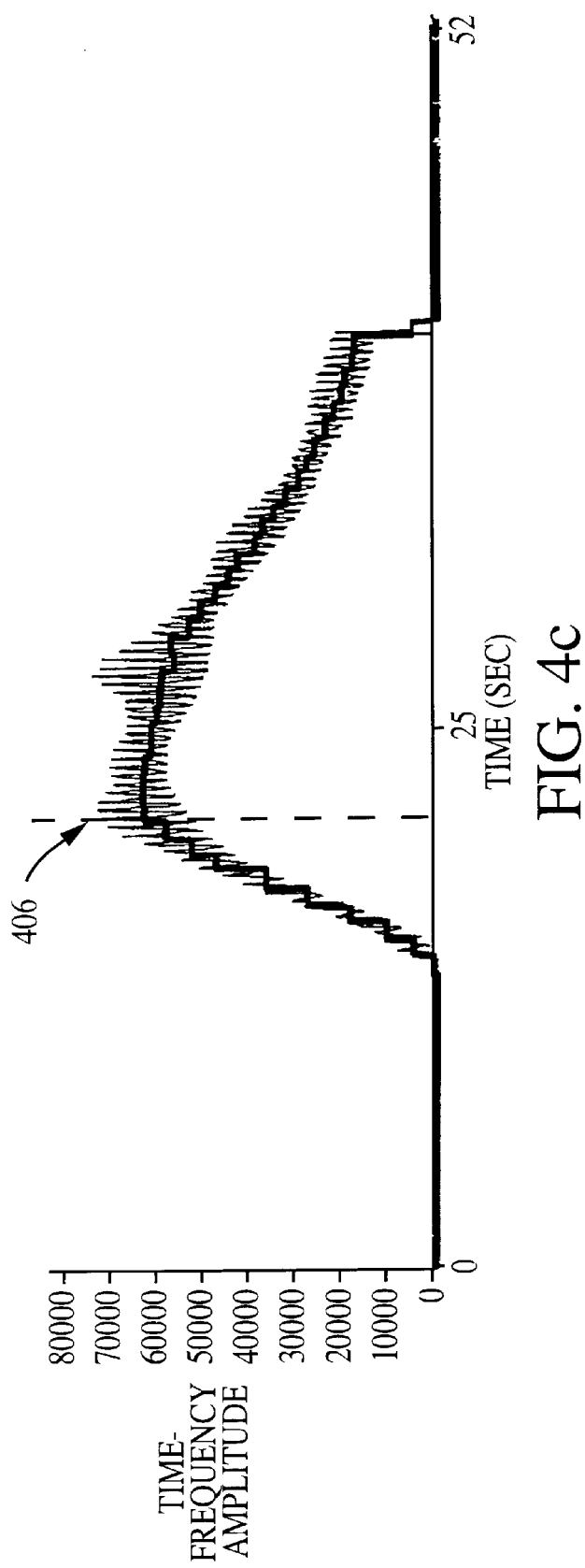

FIGS. 4a–4c are exemplary plots illustrating the relationship between measured radial arterial blood pressure and time (FIG. 4a), radial blood velocity and time (FIG. 4b), and the Pseudo Wigner distribution and time (FIG. 4c), based on typical data obtained using the method of FIG. 3a. The characteristic peak in the Pseudo Wigner distribution results from a large peak trend in the baseline of the blood velocity signal, also known as the end-diastolic velocity (FIG. 4b). In other arteries such as the brachial and femoral arteries, it is known that a similar peak trend in the end-diastolic velocity can be induced after complete arterial occlusion with a cuff for several minutes, followed by complete cuff release. The transient increase in blood flow that follows a brief arterial occlusion is called reactive hyperemia. This transient increase in blood flow and end-diastolic velocity is known to induce a transient increase of 19% in brachial arterial diameter. See, e.g., Anderson, E., et al, "Flow-mediated and reflex changes in large peripheral artery tone in humans", *Circulation*, 79:93–100, 1989, which is incorporated herein by reference in its entirety.

While the radial artery is not compressed by a cuff at the beginning of a decreasing applanation sweep, its flow is completely occluded by the pressure/ultrasound sensor. As the compression decreases during the course of a sweep, reactive hyperemia and its signature peak trend in end-diastolic velocity are induced. The accompanying transient increase in arterial diameter occurs transversely across the artery, but is probably initially prevented sagitally (top to bottom) by the external pressure exerted by the sensor. However, as this external pressure decreases during the sweep to the true mean arterial pressure, the opposing pressure within the artery becomes sufficient that the sagittal arterial diameter may also now increase. The increase in sagital arterial diameter would occur when the transmural pressure equals zero.

The peak in the Pseudo Wigner distribution at a frequency of 0 Hz may indicate when this sudden arterial diameter increase occurs. From Eqn. 1, it is known that the mean blood velocity is proportional to the Doppler shift frequency. The angular frequency of the received wave, $\omega_d$, is found using Eqn. 5:

$$\omega_d = 2\pi f_d, \quad \text{(Eqn. 5)}$$

The angular frequency $\omega_d$ is integrated; this integration results in the phase of the detected signal echo, $\phi$, as illustrated in Eqn. 6:

$$\phi = \int \omega_d dt. \quad \text{(Eqn. 6)}$$

As is well known in the art, the low frequencies in the phase echo are proportional to the relative arterial diameter of the artery, d. See, e.g., Hoeks, A. P. G., et al, "Transcutaneous detection of relative changes in artery diameter" *Ultrasound*

*Med & Biol*, 11:51–59, 1985. The phase φ of the detected echo is a function of the time delay between reflection from the near and far arterial walls. Because the time delay depends only on the time difference between reflections from the two arterial walls, the measurement is insensitive to transmission angle. Note that only the relative arterial diameter changes from an initial diameter value during overcompression can be estimated. The relative arterial diameter d is therefore related to the phase using Eqn. 7:

$$d = \frac{\phi c}{4\pi f_o} = \frac{c}{f_o}\int f_d dt = \cos\theta \int |\bar{v}| dt. \quad \text{(Eqn. 7)}$$

Referring back to the Pseudo Wigner distribution calculation at 0 Hz in Eqn. 4, this discrete summation is equivalent to the continuous integral in Eqn 7. As the constant 2 in Eqn. 4 and cosθ in Eqn. 7 are only scale factors and $u(n) \equiv |\bar{v}(n)|$, the Pseudo Wigner distribution at 0 Hz is equivalent to the proportional squared relative arterial diameter. Therefore, the peak distribution may occur at the sudden change in sagittal arterial diameter when MAP is reached (FIG. 2). The distribution is smooth, rather than discontinuous at the peak, because the time-frequency distribution acts as a smoothing filter.

Figure 3C:
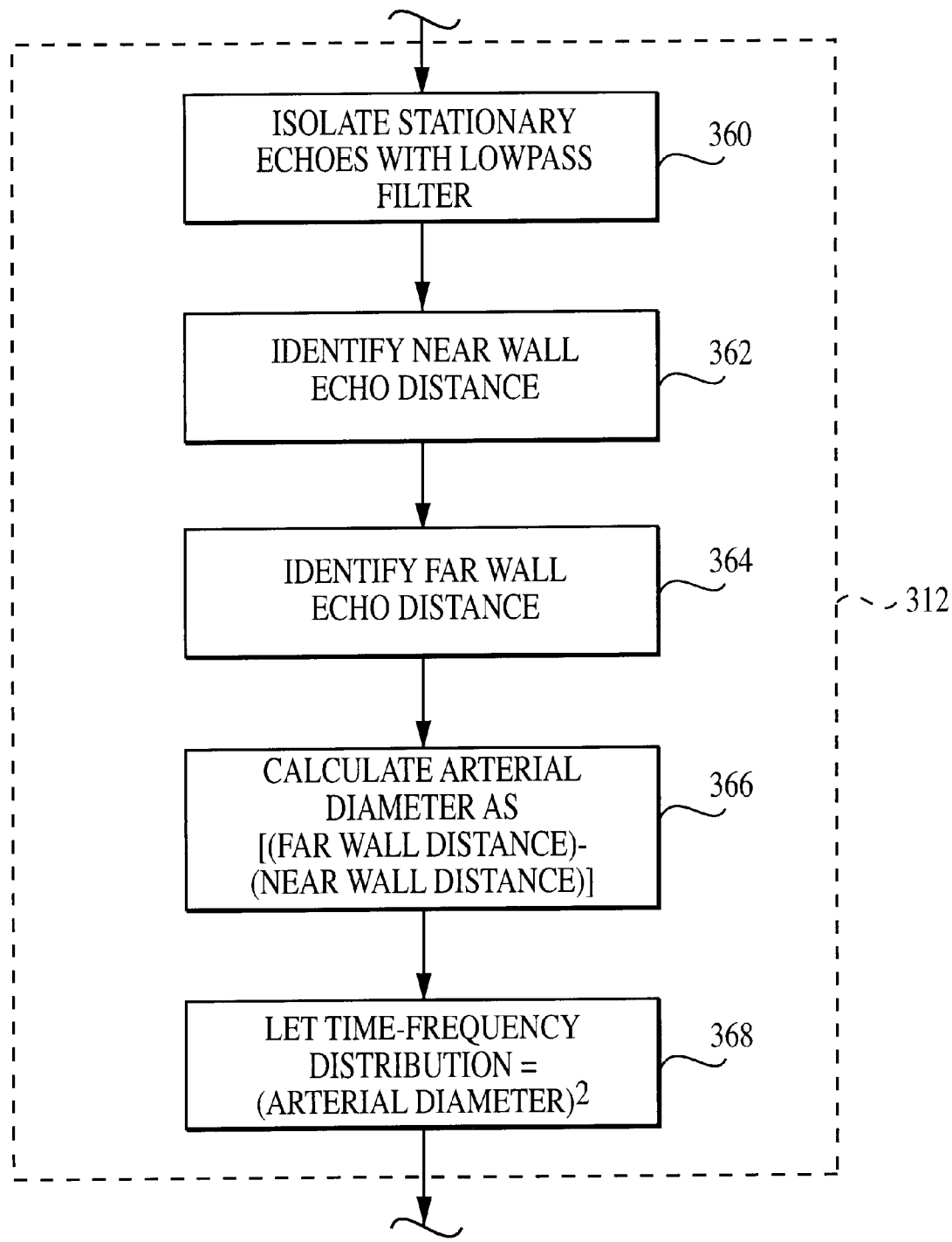
FIG. 3c is a block diagram illustrating a second embodiment of the method of estimating the time-frequency distribution.

Based on this maximum arterial diameter hypothesis, a second embodiment of the method of calculating blood velocity and arterial diameter in conjunction with step 312 of FIG. 3*a* is now described with respect to FIG. 3*c*. Rather than calculate the maximum mean time-frequency distribution, diameter changes can be calculated by monitoring the sagittal near and far walls directly. First, stationary echoes are obtained in step 360 using a lowpass filter. The sagittal near and far wall echoes are identified in steps 362 and 364, respectively, and the distance between them is used to calculate the arterial diameter over time in step 366. Finally, in step 368, the time-frequency distribution is equated to the square of the arterial diameter. Note that while this method of calculating the arterial diameter may detect a sudden diametric change more quickly than the time-frequency based method illustrated in FIG. 3*b*, it is also more complicated because the near and far walls must be continuously detected. See also the discussion of FIGS. 5*a* and 5*b* below, which illustrate two exemplary ultrasound filter circuits useful in performing the analysis of FIG. 3*c*.

It is noted that many variations of the methods described above with reference to FIGS. 3*a*–3*c* may be utilized consistent with the invention. Specifically, certain steps are optional and may be performed or deleted as desired. For example, a discrete frequency other than k=0 may be used in step 322. Similarly, other steps (such as additional data sampling or mathematical analysis for example) may be added to the foregoing embodiments. Additionally, the order of performance of certain steps may be permuted, or performed in parallel (or series) if desired. The foregoing methods of FIGS. 3*a*–3*c* are therefore merely illustrative of the broader methods of the invention disclosed herein.

The application of the method of FIGS. 3*a*–3*b* to typical data is set forth in Appendix A hereto, and illustrated in the exemplary plots of FIGS. 4*a*–4*c*. As shown in FIG. 4*a*, the measured arterial blood pressure 400 generally declines with time, due to reduced applanation of the artery. Note that at some time after beginning the applanation sweep, in this example after approximately 15 seconds, the maximum pulsatile pressure (i.e., the largest peak-to-peak pressure difference) is experienced. At this point, the mean arterial blood pressure (MAP) 402 is approximately 165 mm Hg. At some further time, in this example after approximately 21 seconds, the mean time-frequency distribution (FIG. 4*c*) is maximized, and the MAP 406 (FIG. 4*a*) is approximately 144 mm Hg. At a third time, in this example after approximately 24 seconds, the MAP measured during tonometric applanation 410 is closest to the average MAP measured using a prior art oscillometry device, at 137 mm Hg. Hence, based on the data presented in FIG. 4*a*, prior art maximum pulsatile techniques are substantially less accurate than the "maximum time-frequency" method of the present invention. More significantly, the maximum time-frequency method disclosed herein provides an excellent approximation of the actual mean arterial pressure (as measured by an oscillometry device). Note that noninvasive oscillometry measurement itself possesses an error when compared to the invasive gold standard measurement that utilizes an intra-arterial pressure catheter.

It should also be noted that the "maximum mean time-frequency" method disclosed herein is substantially insensitive to the orientation of the ultrasonic transducer with respect to the artery. As further detailed in Appendix A, numerous anecdotal measurements obtained by the applicant herein showed little variation under a broad range of angular pitch (i.e., rotation around an axis transverse to the longitudinal axis of the artery being measured) and roll (i.e., rotation around the longitudinal axis of the artery) values. It will be readily appreciated that such insensitivity affords great advantages to the user, since consistent results may be obtained with essentially no consideration to the angular position of the tonometric sensor(s).

Referring now to FIGS. 5*a*–5*b*, two exemplary embodiments of the Doppler ultrasound filtering circuit used in conjunction with the method of FIG. 3*c* are described. In the embodiment 500 of FIG. 5*a*, the received signal is amplified, and supplied to a radio frequency (RF) switch 504. The switch gates the signal to the RF mixer 506, which mixes the gated bursts with the original transmission frequency. Through this demodulation scheme, the Doppler shift frequencies are isolated. A lowpass filter of 1 MHz 507 is applied to remove the signal sideband frequencies and noise, although it will be appreciated that other filter frequencies may be used. A bandpass filter 508 with a cutoff frequencies of 300 Hz and 4 kHz is then applied to remove unwanted echoes from stationary tissue such as arterial walls. The output of the bandpass filter is further processed to obtain the mean Doppler shift frequencies.

In the embodiment of FIG. 5*b*, for direct calculation of arterial diameter, this bandpass filter can be replaced by a lowpass filter 510 with a cutoff of 40 Hz that isolates stationary echoes. The near and far walls would be identified from the stationary echoes and used to calculate changes in arterial diameter.

Arterial Blood Pressure Measuring Apparatus

Figure 6:
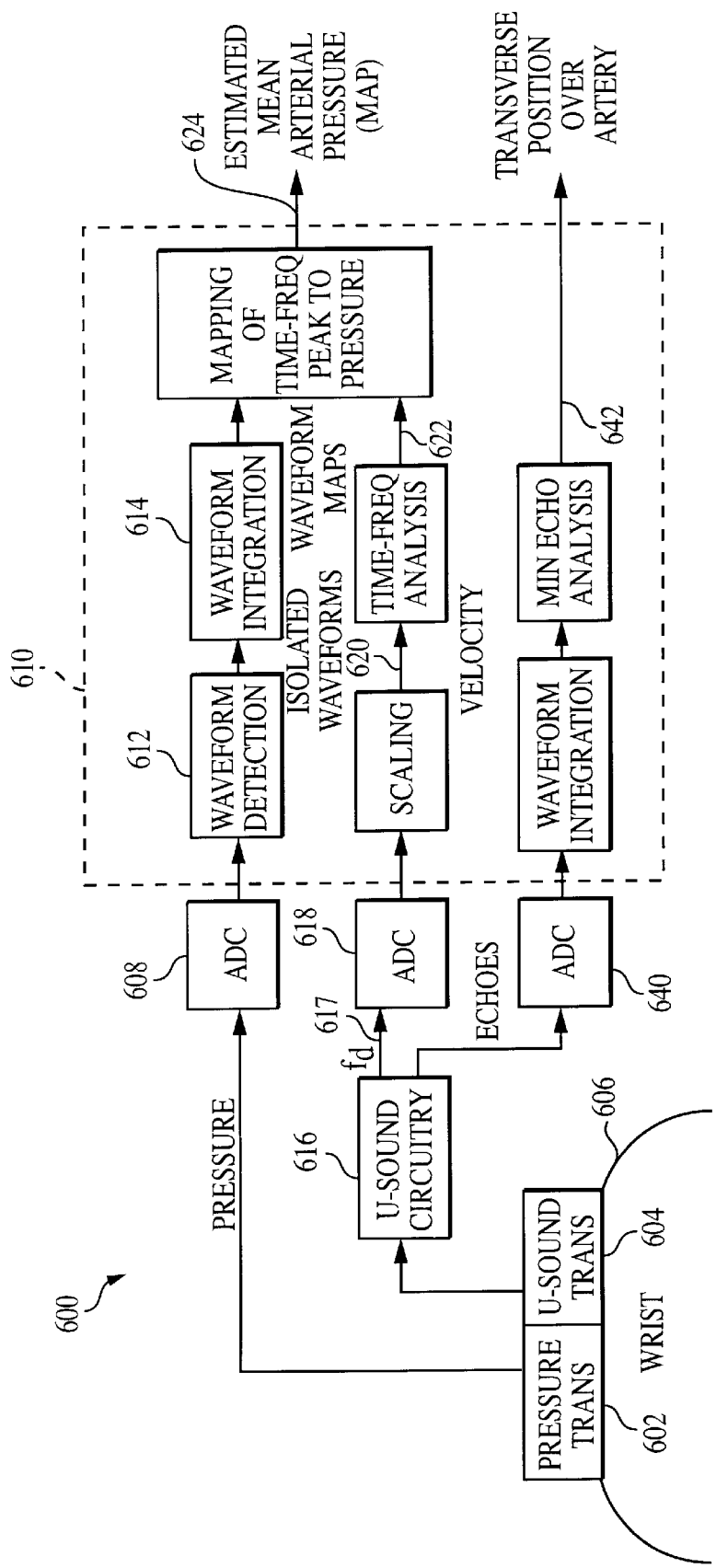
FIG. 6 is a functional block diagram of one embodiment of the arterial blood pressure monitoring device of the present invention.

Referring now to FIG. 6, one embodiment of the blood pressure measuring system according to the invention is described. As shown in FIG. 6, the system 600 comprises pressure and ultrasonic transducers 602, 604 which are placed in contact with the skin of the subject 606 during use. The pressure transducer 602 of the present embodiment is a silicon transducer of the type well known in the electrical arts, although other may be used. It will be recognized that the term "transducer" as used herein is meant to include any type of sensor capable of sensing or receiving one parameter and generating or transmitting a signal based thereon, or alternatively capable of receiving a signal and generating some physical response thereto.

Pressure applied to the face of the transducer is converted to an electrical signal bearing a known relationship thereto.

The pressure transducer 602 is connected to a first analog-to-digital converter (ADC) 608, which converts the analog signal generated by the pressure transducer 602 to a digital representation. In the present embodiment, a 12-bit ADC is used, although it will be appreciated that other types may be substituted. The digitized pressure signal is then supplied to a digital signal processor (DSP) 610. Within the processor, each pressure waveform is detected using wavelet transforms 612. Wavelet transforms are known to those skilled in the art to easily detect edges, or in this case the onset of new waveforms, while noise is present. Each isolated waveform is then integrated to determine its mean arterial pressure value 614.

The ultrasonic transducer 604 generates and transmits an acoustic wave based on a first electrical signal applied thereto, and subsequently generates a second electrical signal upon receiving pressure waves in the form of echoes resulting from the transmitted acoustic waves. The first electrical signal is generated via an ultrasonic driving and receiving circuit 616, which is described in greater detail with reference to FIG. 7. The driving and receiving circuit 616 generates electrical pulses which, when applied to the transducer 604, produce acoustic energy having a frequency on the order of 8 MHz, a pulse width or duration of approximately 8 microseconds, and a pulse repetition interval (PRI) of approximately 16 us, although other values of frequency, pulse width, and PRI may be used. Hence, the transducer 604 of the present embodiment emits an 8 microsecond pulse, which is followed by an 8 microsecond "listen" period, every 16 microseconds. The echoes from these pulses are received by the ultrasonic transducer 604 during the listen period. The ultrasonic transducer 604 of the present embodiment is a ceramic piezoelectric device of the type well known in the art, although other types may be substituted. The transducer 604 converts the received acoustic signal to an electrical signal, which is then supplied to the receiving section of the ultrasonic driver and receiver circuit 616, which contains two receiver circuits. The output of the first receiver circuit is an analog signal representative of the Doppler frequency $f_d$ of the echo received by the transducer 604. The analog output 617 is then converted to a digital representation by a second ADC 618, and supplied to the DSP 610. Within the DSP, the digitized Doppler frequency is scaled to compute the blood velocity 620 within the artery $|v|$ based on the Doppler frequency $f_d$, as described above. The time-frequency distribution of the blood velocity 622 is then computed. Finally, the DSP maps in time the peak of the time-frequency distribution to the corresponding pressure waveform to produce the estimated MAP 624, based on the method of FIG. 3a described above.

The output of the ultrasonic receiver circuit 616 is an analog echo signal proportional to absorption of the transmitted frequencies by blood or tissue. This analog signal is converted to a digital representation by a third ADC 640 and supplied to the DSP 610. Within the DSP, each group of echoes, generated for a different transversal position, is integrated to determine a mean value 642. The mean echo values are compared to determine the minimum value, which is caused by direct positioning over the artery.

The use of such algorithms running on digital signal processing devices (such as the DSP 610) to perform mathematical calculations is well known in the signal processing arts, and accordingly will not be described further herein. The DSP's output signal is then converted to a form useful to the user such as a digital or analog display, computer data file, or audible indicator.

Figure 7:
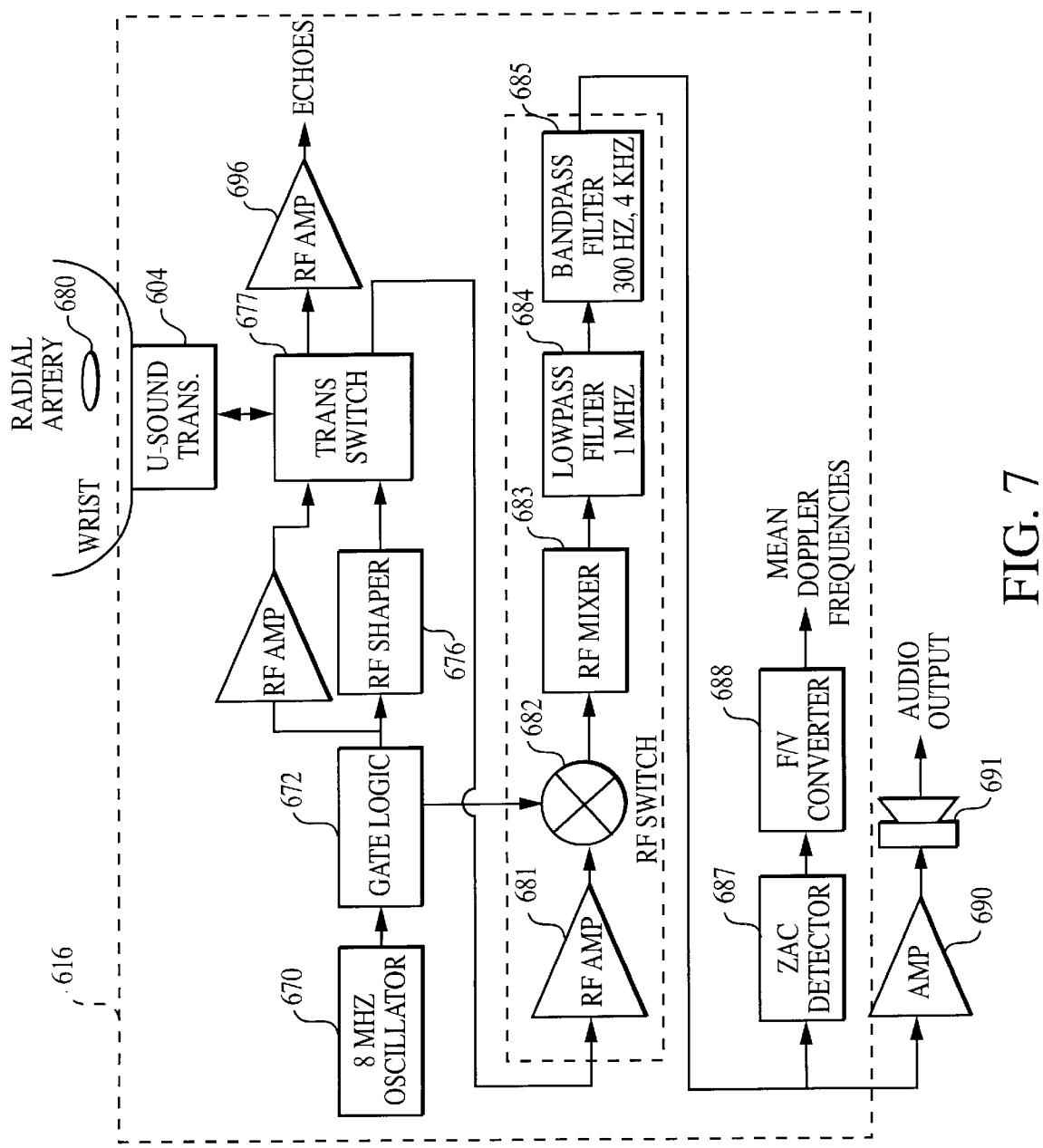
FIG. 7 is a block diagram of one embodiment of the ultrasound receiver circuit used in conjunction with the blood pressure monitoring device of FIG. 6.

Referring now to FIG. 7, which incorporates the ultrasonic filtering circuit of FIG. 5a, one embodiment of the ultrasonic driver and receiver circuit 616 is now described. As shown in FIG. 7, an oscillator 620 generates a continuous square wave signal, having a fixed frequency of 8 MHz, for coupling to a gate logic circuit 672 and to an RF mixer 674. The gate logic circuit transmits 8 us bursts of the 8 MHz signal, interrupted by 8 microsecond dead times. An RF shaper circuit 676 converts the resulting series of square wave bursts from the gate logic circuit 672 into corresponding sine wave bursts, for application through a transducer switch 677, to the ultrasonic transducer 604. The transducer switch 677 routes ultrasonic signals for both applanation and transverse positioning. The ultrasonic transducer 604 is thereby conditioned to transmit a succession of 8 MHz bursts of sonic energy into the adjacent wrist tissue.

In use, the transmitted bursts of sonic energy are scattered by red blood cells flowing through the subject's radial artery 680, and a portion of the scattered energy is directed back toward the ultrasonic transducer 604. The time required for the return energy to reach the ultrasonic transducer varies according to the speed of sound in the tissue and according to the depth of the artery. Typical transit times are in the range of 6 to 7 microseconds.

The ultrasonic transducer 604 is used to receive the reflected ultrasound energy during the dead times between the successive transmitted bursts. For the applanation application, the ultrasonic transducer therefore produces a received signal, of relatively low magnitude, and this received signal is coupled to an RF amplifier 681 for amplification. The amplified signal is then supplied to an RF switch 682, which gates the signal to the RF mixer 683 only during the dead times between successive transmitted bursts. The RF mixer 683 mixes these gated bursts with the original 8 MHz signal received from the oscillator.

The frequency of the ultrasonic transducer's transmit signal will differ from that of the return signal, because the scattering red blood cells within the radial artery are moving. Thus, the return signal, effectively, is frequency modulated by the blood flow velocity. The signal output by the RF mixer 683, therefore, will incorporate the 8 MHz fundamental frequency, as well as sum and difference frequencies of the transmit and return signals. This output signal is supplied to a lowpass filter 684 with cutoff frequency of 1 MHz, for removal of the 8 MHz fundamental frequency, as well as any higher-order harmonics from the difference frequencies. A bandpass filter 685 that ranges from 300 Hz to 4 KHz then removes all signal components other than those components representing the actual blood velocity.

The signal output from the bandpass filter 685 is supplied to a zero-axis crossing detector 687, which functions to produce a pulse each time the signal crosses a zero axis. These pulses are supplied to a frequency-to-voltage converter circuit 688, which produces a DC output signal indicative of the mean Doppler frequencies. The signal output by the bandpass filter 685 is also supplied to an audio amplifier 690, and in turn to a speaker 691, to enable an operator to hear a representation of the Doppler signals and thereby to determine when the transducer is located approximately over the radial artery.

The output of the gate logic circuit is also amplified via an amplifier 694, and when transverse positioning is desired, switched to the ultrasonic transducer 604. The received echoes are coupled to an RF amplifier 696 and output for further processing to determine minimum echo value as a function of position.

It is noted that while the embodiment of FIGS. 5a and 7 utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 604) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to fall within the scope of the claims appended hereto.

Figure 8:
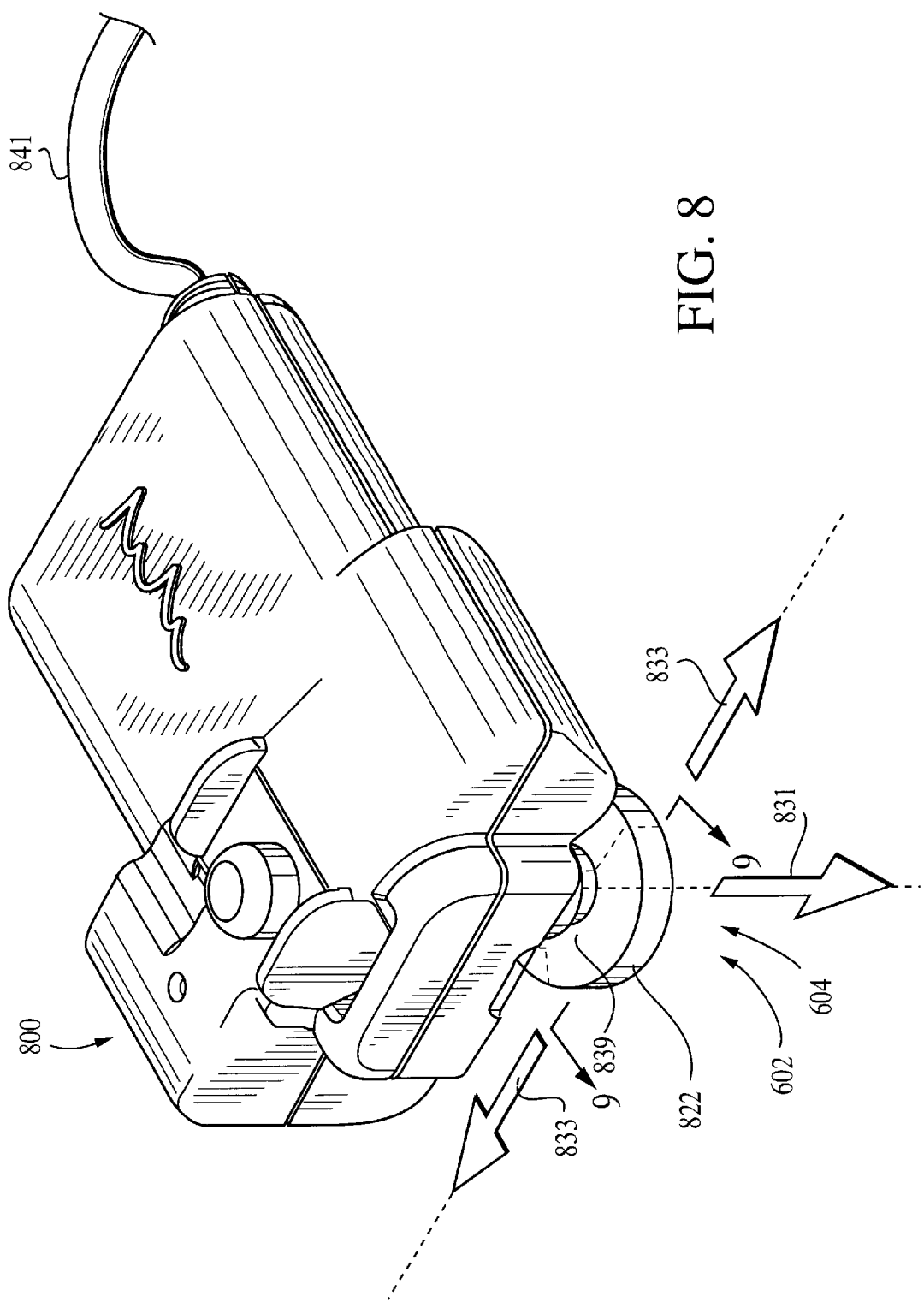
FIG. 8 is a perspective view of one embodiment of the applanation and transverse positioning assembly of the invention.
Figure 9:
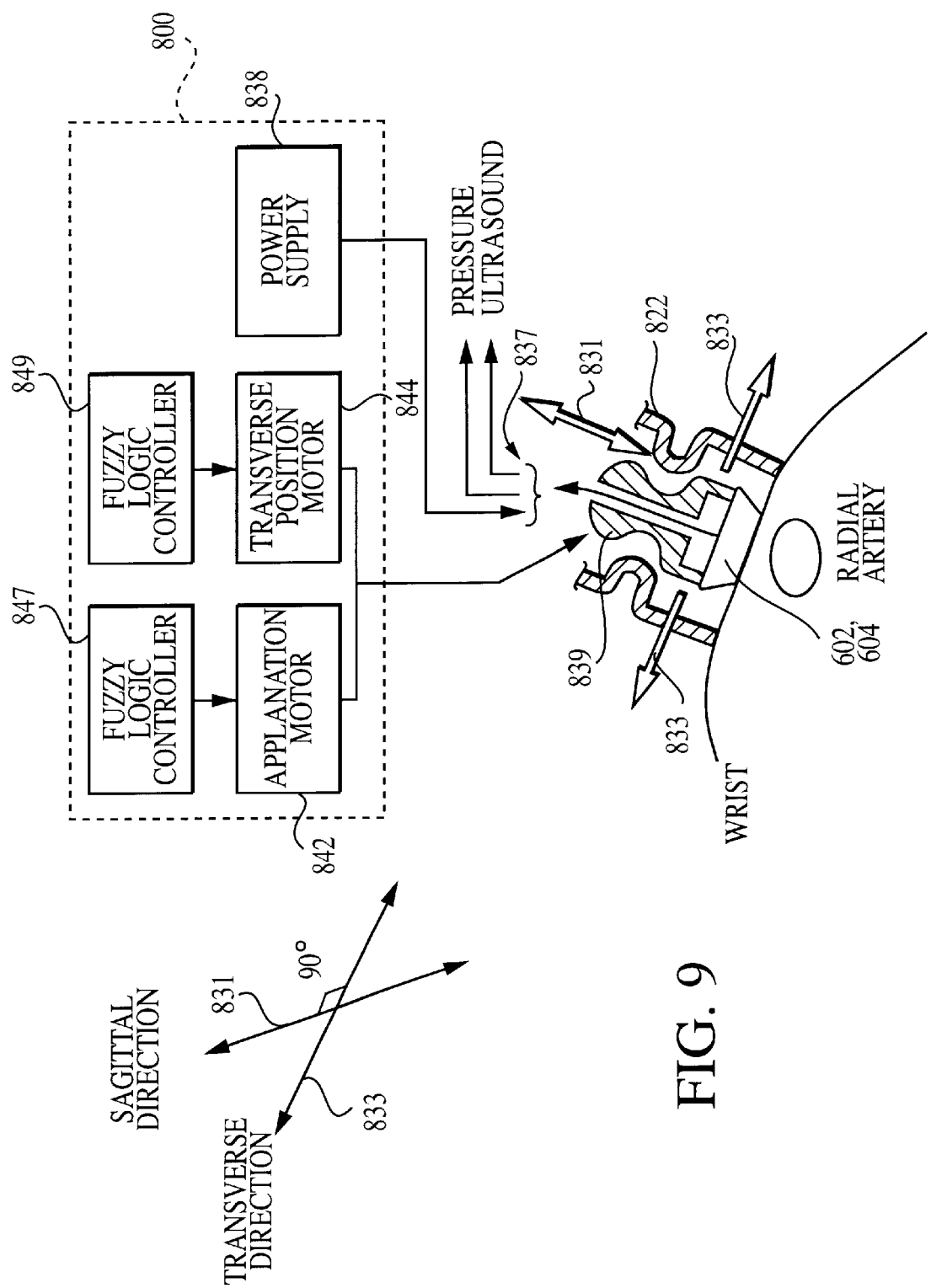
FIG. 9 is a cross-sectional view, including functional block diagram, of the blood pressure measurement system of the invention, taken along lines 9—9 of FIG. 8.

Referring now to FIGS. 8 and 9, one embodiment of the applanation and transverse positioning device 800 of the invention is illustrated. The device 800 is adapted to receive a transducer housing element 822 in the lower extensive portion 801 thereof. The transducer housing element contains the aforementioned pressure and ultrasonic transducers 602, 604 therein, the latter physically being combined into a single transducer element, although other configurations including a tandem ultrasonic/pressure configuration (not shown), or an array of multiple pressure and/or ultrasonic transducers, may be used. The transducers 602, 604 are free to move within the housing 822 in the sagittal direction 831 and the transverse direction 833 with respect to the artery, as driven by the applanation and positioning motors 842, 844. The housing element 822 of the present embodiment contacts the wrist skin circumferentially around the transducers 602, 604 which move with respect to the housing element 822 and the skin, although it will be appreciated that a variety of different configurations and methods may be used. For example, a substantially compliant housing which conforms to the tissue of the subject, yet allows the transducers 602, 604 to move in the desired directions within an aperture therein, may be substituted. When adhered to the wrist using the wrist brace disclosed herein in FIG. 10 (or other retaining mechanism), the active surface 810 of the transducers 602, 604 is in variable contact with the skin of the wrist, and roughly flush with the bottom edge of the housing element 822. The top of the transducers 602, 604 include an electrical connection 837 to the power supply 838 of the applanation and transverse positioning assembly 800, as well as to circuitry for processing the pressure and ultrasound signals from the transducers. The transducers are also coupled via a mechanical connection 839 to the motors of the applanation and transverse positioning assembly 800, such that the position of the transducers 602, 604 is varied in the sagittal and transverse directions by the applanation and transverse positioning motors 842, 844, respectively. While a ball-and-socket arrangement is illustrated for the mechanical connection 839 between the transducers 602, 604 and the motors, it will be appreciated that a variety of different arrangements (such as an articulated joint or sliding coupling) may be used. Collectively, the housing element 822 and the applanation and transverse positioning assembly 800 comprise a coupling device, which maintains the transducers 602, 604 properly coupled to the subject's wrist when mounted in the wrist brace of FIG. 10. The transducers 602, 604 move in the sagittal direction 831 within the housing element 822 as urged by the applanation motor 842 so as to compress the radial artery to varying degrees during blood pressure measurement. The transverse positioning motor 844 moves the transducers in the transverse direction 833 within the housing element 822 during transverse positioning (described below). In the present embodiment, the applanation motor is controlled by a fuzzy logic control circuit 847 of the type well known in the art so as to perform applanation sweeps, which vary the degree of arterial compression, although other control schemes may be used. For example, the applanation of the artery may be performed so as to maintain the transmural pressure at or near zero. Alternatively, the applanation motor may be modulated by the control circuit in a periodic or continuous fashion such that the artery is compressed according to a desired profile, such as a sinusoid. Such control and modulation schemes are described in Applicant's two co-pending U.S. Pat. applications, numbered Ser. Nos. 09/120,069 and 09/120,205, both entitled "Apparatus and Method for Non-Invasively Monitoring a Subject's Arterial Blood Pressure" and filed Jul. 20, 1998, which are incorporated herein by reference in their entirety.

The transverse positioning motor 844 of the assembly 800 is used to position the transducers 602, 604 directly over the artery of interest. Specifically, the ultrasonic emissions of the ultrasonic transducer 604 are substantially normal to the surface of the subject's skin and are used to generate echoes, which are reflected from the blood and tissues. These echoes are received by the transducer 604 and analyzed so as to determine their amplitude as a function of transverse position of the transducer over the artery. As with the applanation motor 842 described above, the transverse positioning motor 844 is controlled via a fuzzy logic control circuit 849 which signals the motor 844 to adjust the transverse position of the transducer such that the amplitude of the echoes (and SNR) is optimized. Alternatively, the user may manually position the transducer 604 using manual control circuitry based on an indication of the relative strength of the blood velocity echoes, such as may be provided to the user by an audible or visual representation thereof. For example, the audio output of the speaker 691 (FIG. 7), whose frequency is proportional to the amplitude of the received echoes, may be used to position the transducer 604. Many such control schemes for the transverse positioning motor are possible, all being within the scope of the claims appended hereto.

Figure 10:
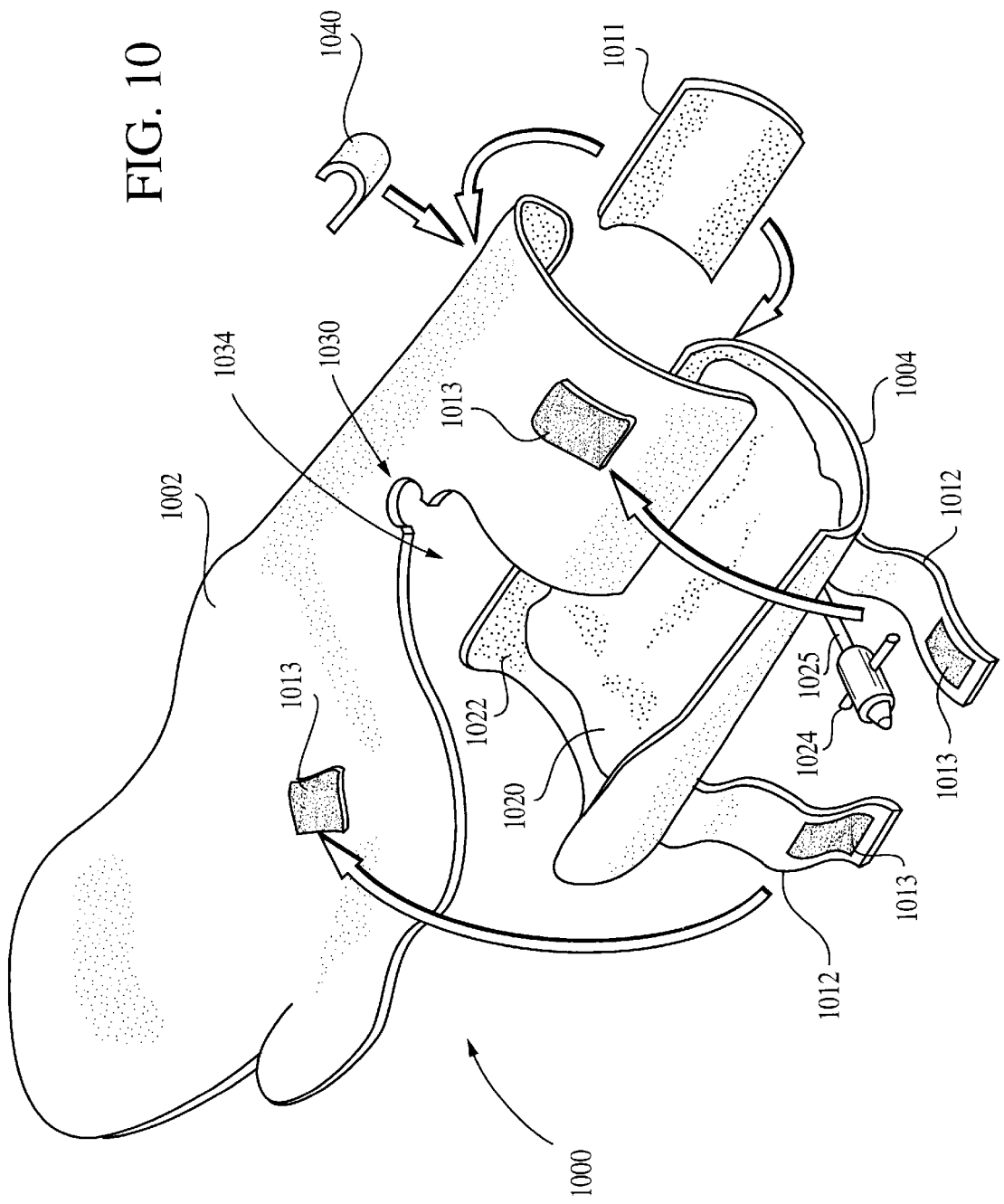
FIG. 10 is an exploded perspective view of one embodiment of the wrist brace of the present invention.
Figure 11:
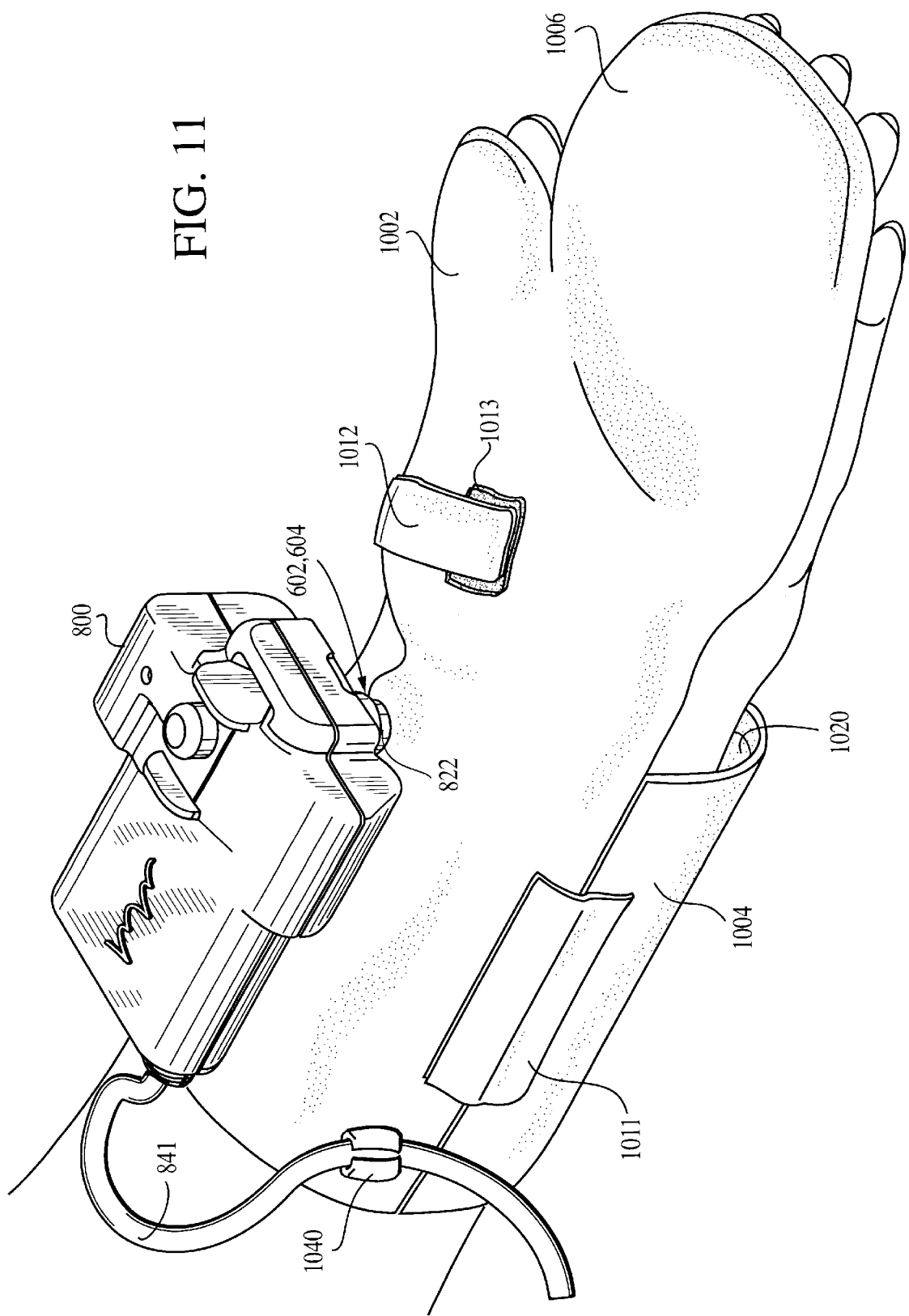
FIG. 11 is a perspective view of the wrist brace of FIG. 10 shown fitted to the wrist of a subject, and having the applanation and positioning assembly of FIG. 8 mounted thereon.

Referring now to FIGS. 10 and 11, the wrist brace 1000 of the invention is now described. In the embodiment of FIG. 10, the brace 1000 comprises an upper brace element 1002 and lower brace element 1004, which are adapted to fit the inner and outer wrist surfaces of the subject, respectively. As used herein, the terms "upper" and "lower" and "inner" and "outer" are merely descriptive of the orientation of the brace elements 1002, 1004 as illustrated in FIG. 10, and are in no way limiting as to the position or use of the brace. The upper brace element 1002 includes an extending portion 1006, which receives the inner surfaces of the subject's hand, as best shown in FIG. 11. The extending portion 1006 is contoured such that the subject's hand is retained in a natural, relaxed position, thereby increasing the time that the brace 1000 may be worn without discomfort. The upper and lower elements 1002, 1004 are joined on one common edge by a flexible fabric or polymer hinge 1011 which is fastened to both elements 1002, 1004. One or more straps 1012 are also fitted to the upper and lower elements 1002, 1004 such that when the brace 1000 is fitted to the subject's wrist and hand, the straps 1012 permit the upper and lower elements to be secured together firmly. In the present embodiment, the straps 1012 include fasteners 1013 such as Velcro tabs, although other arrangements such as mechanical clasps, snaps, slings, adhesives, or the like may be used. Likewise, the straps 1012 may be replaced partially or entirely with clasps or other similar fastening devices. It will be recognized that literally any means of maintaining the upper brace element 1002 in a substantially fixed position with respect to the lower brace element 1004 may be substituted for the straps 1012 shown in FIGS. 10 and 11.

The upper and lower brace elements 1002, 1004 are advantageously formed using a partially flexible polymer material, thereby allowing for low manufacturing cost, excellent ruggedness, and some degree of compliance with the shape of the subject's tissue. Note, however, that sufficient rigidity of these components is required to accommodate the reaction forces generated by the applanation and transverse positioning assembly 800 shown in FIG. 8 above. Specifically, the applanation and transverse positioning assembly 800 is rigidly mounted to the upper brace element 1002, as shown in FIG. 11. In one embodiment, the housing element 822 fits within an opening 1034 formed within the upper brace element 1002 adjacent to the recess 1030 such that the assembly 800 can be easily placed and "snapped into" wrist brace 1000. In a first alternative embodiment (not shown), the housing element 822 is formed within the upper brace element 1002 such that the transducers 602, 604 fit within a central aperture formed within the element 822, and the applanation and positioning assembly 800 snaps on to the outer portion of the upper brace element 1002 directly above the transducer housing element 822. In a second alternative embodiment (not shown), the applanation and positioning assembly 800 is formed directly within the upper brace element 1002. In a third alternative embodiment (also not shown), the transducer elements 602, 604 and housing element 822 are disposed within the brace 1000, with the applanation and transverse positioning assembly 800 being removably mounted thereon. It will be recognized that many other alternative configurations are possible.

The electrical cabling 841 associated with the assembly 800 is also optionally received within a routing clip 1040 mounted on the exterior of the upper brace element 1002, thereby reducing the mechanical stress on the rigid mount 846 from the cabling 841 to some degree.

The lower brace element 1004 of the present embodiment also optionally includes an inflatable bladder 1020, which is received within and fastened to the interior surface 1022 of the lower brace element 1004. The bladder 1020 is formed of a flexible material (such as a plastic or rubber) so that it can comply with the shape of the subject's wrist, and accommodate varying degrees of inflation. As used herein, the term "inflation" is meant to include inflation of the bladder 1020 by gaseous and/or liquid substances. The bladder 1020 includes a stopcock 1024 and tube 1025, which allow the user to adjust the inflation of the bladder 1020 when required. The bladder may also be connected to an automatic inflation regulating system (not shown), which dynamically adjusts the inflation of the bladder 1020 to maintain optimal positioning and/or comfort for the subject. Alternatively, the bladder 1020 may be replaced by a substantially compliant pad (not shown), such as one made of foam rubber, which will at least partially adapt its shape to that of the subject's wrist, yet maintain the wrist firmly within the brace. It can be appreciated that many such alternative embodiments are possible.

Referring again to FIG. 11, the installation and positioning of the embodiment of FIGS. 8–10 is described. The wrist brace 1000 is first fitted to the arm of the subject by the clinician such that the opening 1034 and recess 1030 in the upper brace element 1002 are located roughly atop the pulse and the radial artery. The bladder 1020 is adjusted as needed to firmly maintain the position of the brace 1000. Next, the applanation and transverse positioning assembly 800 is snapped into the recess 1030, retaining it in position. The clinician verifies that the bottom of the housing element 822 is touching the skin of the subject's wrist, and is oriented roughly normal to the wrist tissue. The electrical cabling 841 is snapped into the routing clip 1040 as well. Lastly, the ultrasonic transducer (not shown) is energized and a signal applied thereto such that acoustic waves are transmitted into the artery and surrounding tissue; echoes resulting from reflection of these waves off of the blood velocity are used (as previously described) to drive the transverse positioning control circuit and motor so as to optimize the placement of the transducer over the artery. Applanation sweeps of the artery may then be conducted, as described with respect to FIG. 3a herein.

Estimation of Catheter Systolic and Diastolic Pressures Using a Scaling Factor

Referring now to FIGS. 12–18, the method and apparatus for estimating the catheter systolic and diastolic blood pressures is described.

Figure 12:
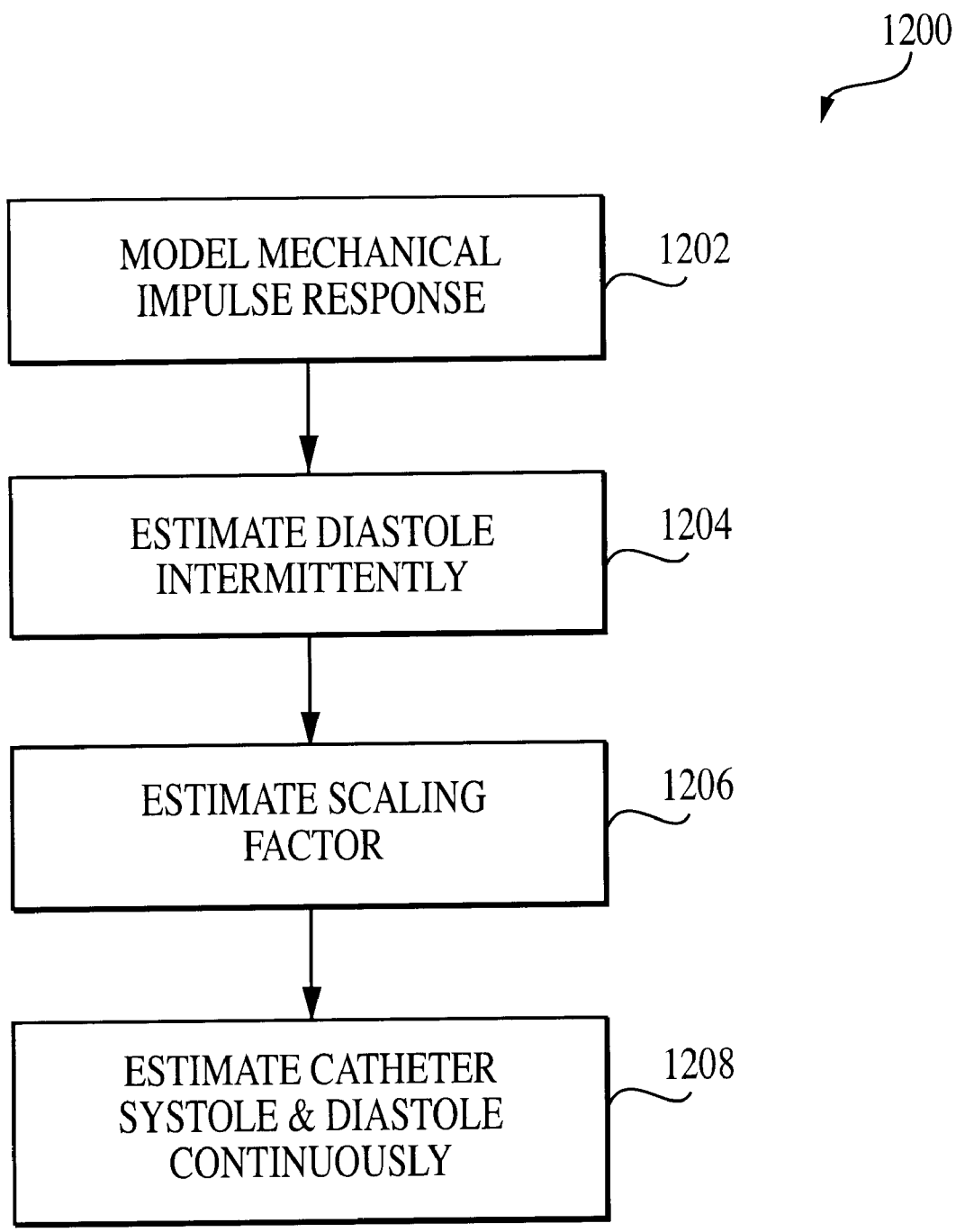
FIG. 12 is a block diagram illustrating one exemplary embodiment of the method of estimating catheter systolic and diastolic blood pressures according to the invention.

As illustrated in FIG. 12, the method 1200 generally comprises the steps of: modeling a mechanical impulse response within the subject per step 1202; estimating diastolic pressure intermittently per step 1204; estimating a scaling factor between the sensed and catheter pressure waveform per step 1206, and estimating the catheter systolic and diastolic blood pressures continuously per step 1208. These steps are described in greater detail with reference to FIGS. 13–18 below.

Mechanical Impulse Response

A mechanical impulse response exists between the true invasive or "catheter" arterial pressure and the tonometric pressure sensed at the radial artery as previously described; i.e., when the artery has been sufficiently compressed or applanated such that the sensed mean arterial pressure (MAP) equals the true MAP. To analyze the nature of this mechanical impulse response (step 1202 of FIG. 12), the impulse response is modeled as a linear controlled, autoregressive (ARX) model of the type known in the mathematical arts as illustrated in Eqn. 8.

$$\sum_{i=0}^{N} a_i y_{servo}(n-i) = \sum_{i=0}^{M} b_i u(n-i), \qquad (8)$$

where:
n=a discrete time sample,
u(n)=the catheter arterial pressure,
$y_{servo}(n)$=the pressure from a sensor positioned at the radial artery with sufficient pressure applied so that the sensed MAP equals the catheter MAP,
$a_i$=feedback coefficient,
$b_i$=feedforward coefficient,
N=number of feedback coefficients and model order, and
M=number of feedforward coefficients.

Figure 13:
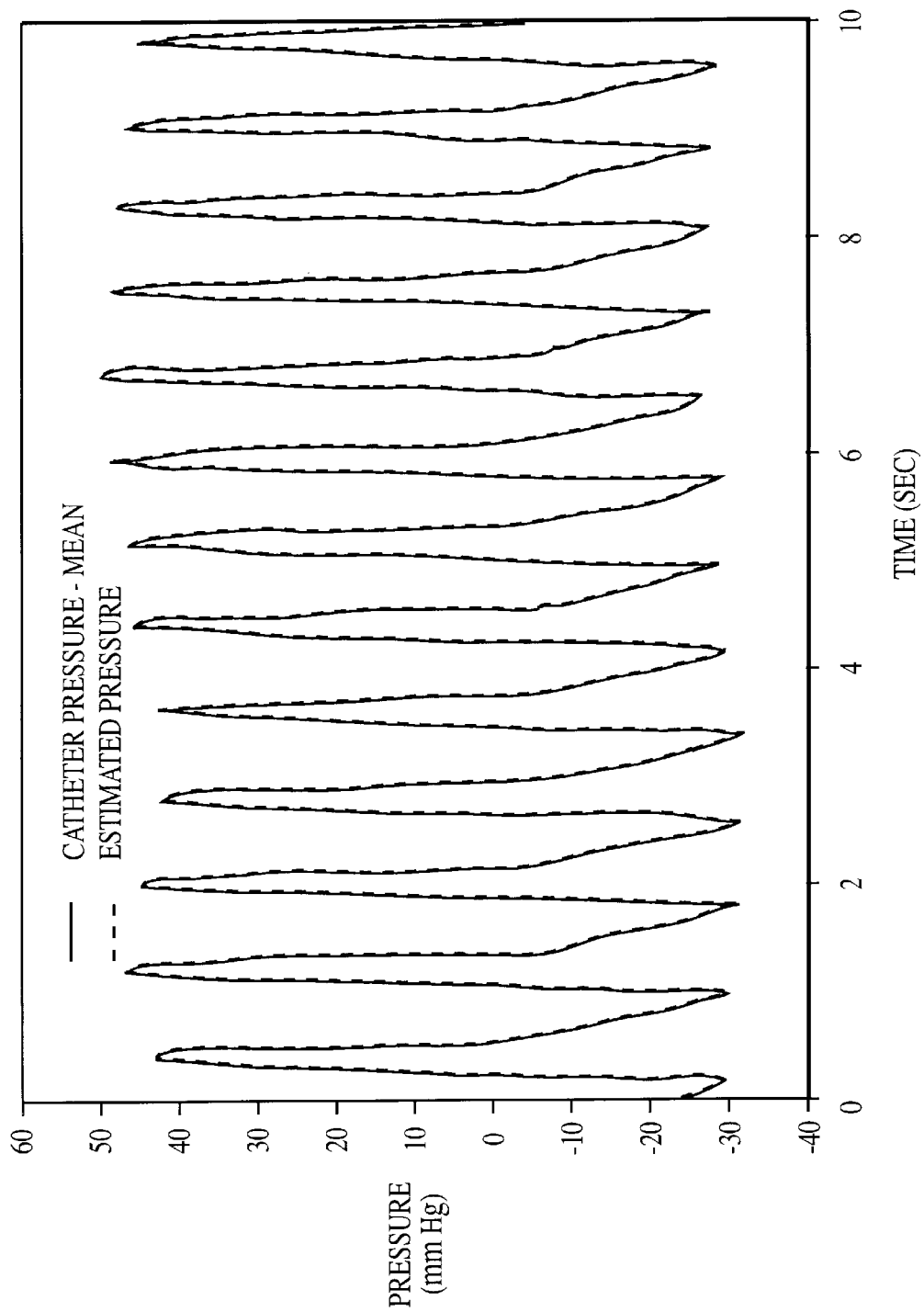
FIG. 13 is a graph illustrating the relationship between estimated catheter pressure (using zeroeth order linear autoregression model) and actual measured catheter pressure for a typical subject.

In this model, $a0$ is chosen to be equal to 1, although other values may be used. The mean arterial pressure values obtained from the subject(s) are subtracted from their respective data sets, and fit to the ARX model, using various combinations of N and M. The optimum model order N is determined using standard criteria well known to those skilled in the art. Specifically, in the illustrated embodiment, the Akaike Final Prediction Error Criterion, standard deviations associated with identified parameter estimates (precision of estimates), and residuals between the estimated and catheter waveforms are used, although it will be recognized that other criteria may be substituted. In the present embodiment, a zeroeth order model with one feedforward coefficient is chosen. Appendix B provides exemplary anecdotal data illustrating the foregoing process. FIG. 13 graphically illustrates the fit between the catheter data and the aforementioned zeroeth order model for an exemplary subject (subject No. 2 from Appendix B).

The results of Applicant's anecdotal testing as described in Appendix B hereto indicate that the pressure sensed at the radial artery may be attenuated by a significant fraction in comparison to catheter pressure. However, while energy is lost due to the aforementioned mechanical impulse response, the catheter frequency characteristics are preserved. Therefore, the catheter systolic and diastolic pressures may advantageously be estimated using a single derived scaling factor (step 1206 of FIG. 12). In the present embodiment of the invention, this scaling factor is derived by first estimating the catheter mean and diastolic pressures, and then calculating the attenuation based on the difference between i) the estimated mean pressure minus the estimated diastolic pressure, and ii) the measured mean pressure minus the measured diastolic pressure. The estimated mean is determined by the time-frequency method and apparatus as previously described herein. Similarly, an estimate of diastolic pressure is obtained by processing the blood velocity waveforms during a decreasing applanation sweep to determine a corresponding pressure waveform whose mean corresponds to an estimate of the true diastolic pressure. The "measured" values are obtained through servo operation around the mean, as described in greater detail below.

Estimate of Diastolic Pressure

Referring now to FIGS. 14a–16, the method of estimating diastolic pressure according to the invention is described. FIGS. 14a–14d illustrate arterial pressure, blood velocity, time frequency signal and wavelet transform respectively as a function of sample number (time). As indicated above, an estimate of diastolic pressure is obtained by processing the blood velocity waveforms during a decreasing applanation sweep to determine a corresponding pressure waveform whose mean corresponds to an estimate of the true diastolic pressure. It has been observed that during the course of this decreasing applanation sweep such as that illustrated in FIG. 14a, the blood velocity contains an end-diastolic component that transiently rises and falls; see FIGS. 14b and 14c. This feature of the velocity may be related to the changes in flow characteristics or changes in arterial diameter. In particular, the time 1402 at which the end-diastolic velocity first "settles" to its final value after transiently increasing (i.e., "settling point") can indicate when the mean pressure applied externally above the radial artery is an estimate of the true diastolic pressure within the artery.

Figure 15:
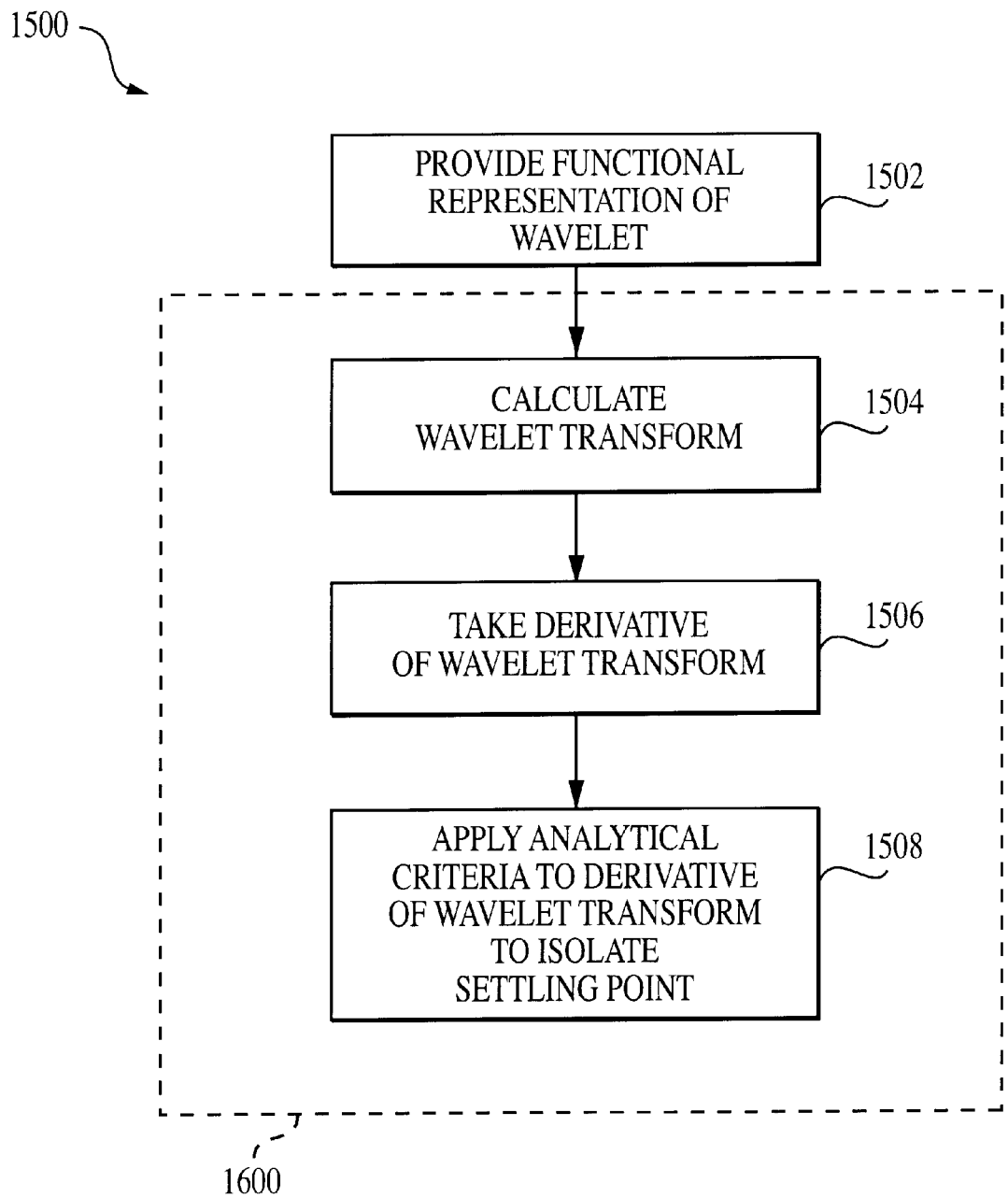
FIG. 15 is a block diagram illustrating one exemplary embodiment of the method of estimating diastolic blood pressure according to the invention.

In general, the process of mathematically isolating this settling point in the time domain is complex, yet can be simplified through processing in the time-scale domain. The generalized method of isolating the settling point according to the invention is illustrated in FIG. 15. As shown in FIG. 15, the method 1500 comprises providing a functional representation of a wavelet in step 1502; calculating a transform of the wavelet in step 1504; taking a derivative of the wavelet transform in step 1506; and applying a set of analytical criteria to the derivative of the wavelet transform in order to isolate the setting point in step 1508.

Figure 16:
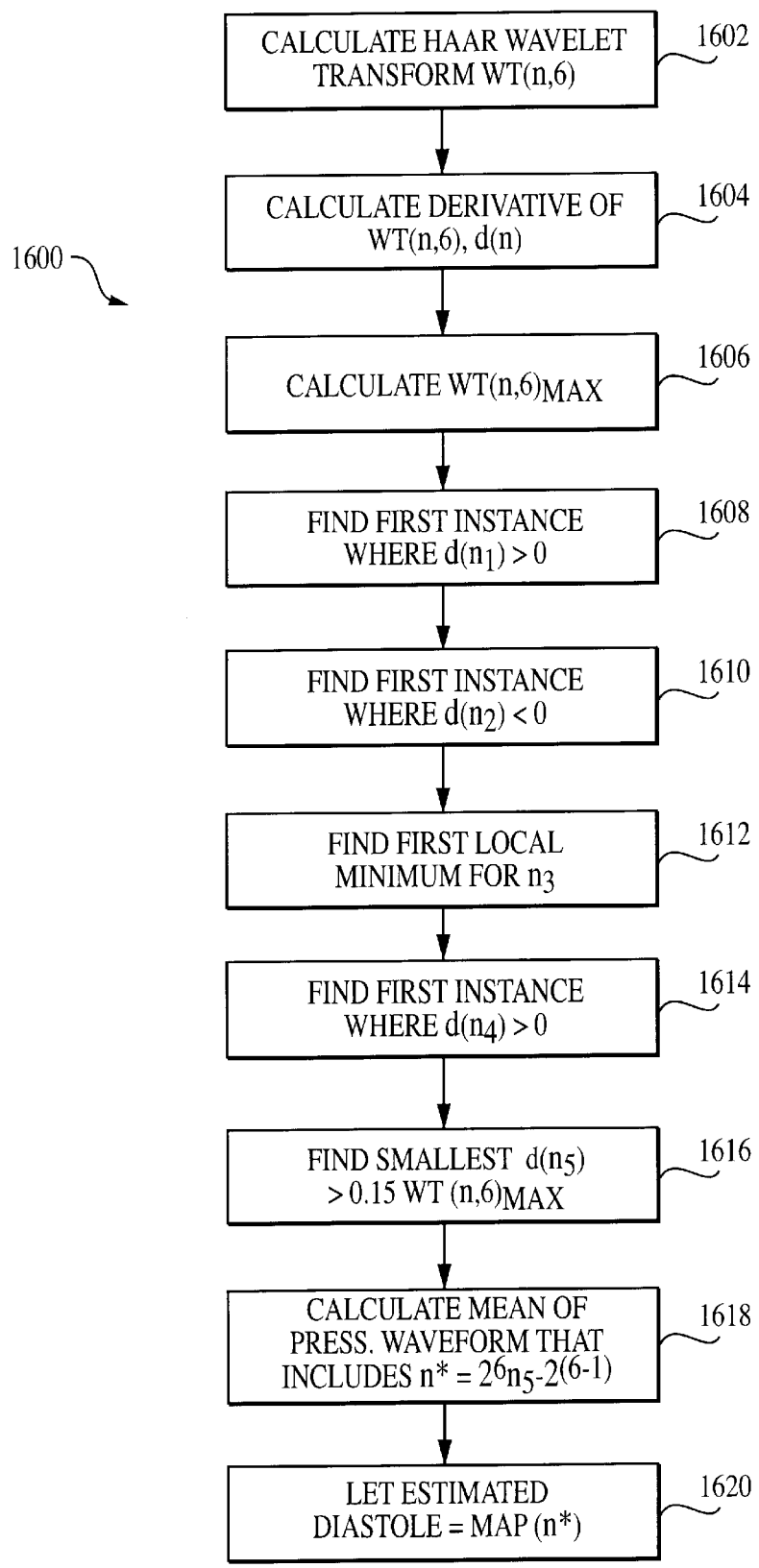
FIG. 16 is a block diagram illustrating one exemplary embodiment of the method of isolating the "settling point" within an applanation sweep according to the invention.

FIG. 16 illustrates one specific embodiment of the method 1500 of isolating the settling point. In this embodiment, the approximation coefficients of a Haar wavelet transform of scale 6 are calculated in order to enable the essential features of the end-diastolic velocity to be isolated. This transform, WT(n,6), is calculated in step 1602 as set forth in Eqn. 9 below:

$$WT(n, 6) = \frac{1}{2^6} \sum_{j=0}^{L-1} x(j)\phi_h\left(\frac{j-h}{2^6}\right), \quad (9)$$

where x(n) is the blood velocity signal, L is the length of the signal (i.e., the total number of samples in the blood velocity signal), and $\phi_h(n)$ is the Haar scaling function as is well known in the mathematical arts. The Haar scaling function is defined as $$\phi_h(n) = \begin{cases} 1, & 0 \le k < 1 \\ & \text{otherwise} \end{cases}. \quad (10)$$

Figure 14A:
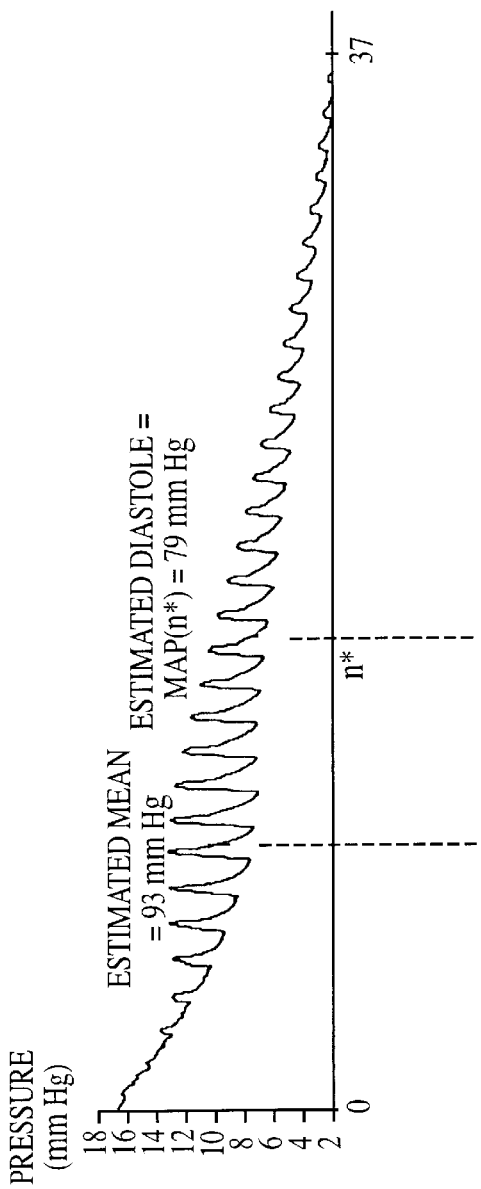
FIGS. 14a–d are graphs representing the estimated arterial blood pressure, blood velocity, time-frequency distribution, and wavelet transform/derivative, respectively, of a typical test subject.
Figure 14B:
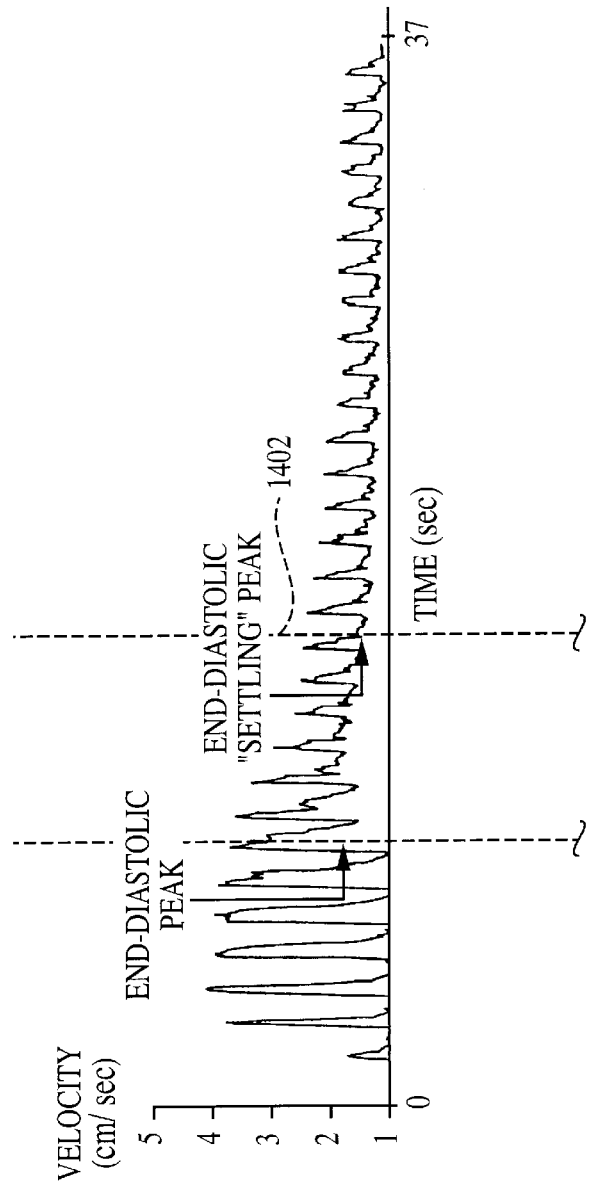

Note that the length of the wavelet transform is $\frac{1}{2^6}=\frac{1}{64}$ the length L of the input signal. Hence, in essence, the transform functions as a low pass filter as illustrated in FIGS. 14b and 14d.

Next, to isolate the settling point, the derivative of the wavelet transform, d(n), is calculated and processed in step 1604 of FIG. 16. First, $WT(n,6)_{max}$ is calculated in step 1606. Next, starting with the first sample, the first instance where the derivative $d(n_1)$ is greater than zero ($d(n_1)>0$) is found in step 1608. Starting with sample $n_1$, the first instance where $d(n_2)<0$ is then found per step 1610. Starting from sample $n_2$, the first local minimum at sample $n_3$ is found in step 1612. In step 1614, and starting from sample $n_3$, the first instance where $d(n_4)>0$ is found. Next, in step 1616, the smallest value of $d(n_5)>0.15\ WT(n,6)_{max}$ is found within the range $n_3<n<n_4$. The mean of the pressure waveform that includes sample $n^*=2^6 n_5-2^{6-1}$ is then calculated in step 1618. The estimated diastolic pressure is then determined as the value of MAP($n^*$) in step 1620.

Figure 14C:
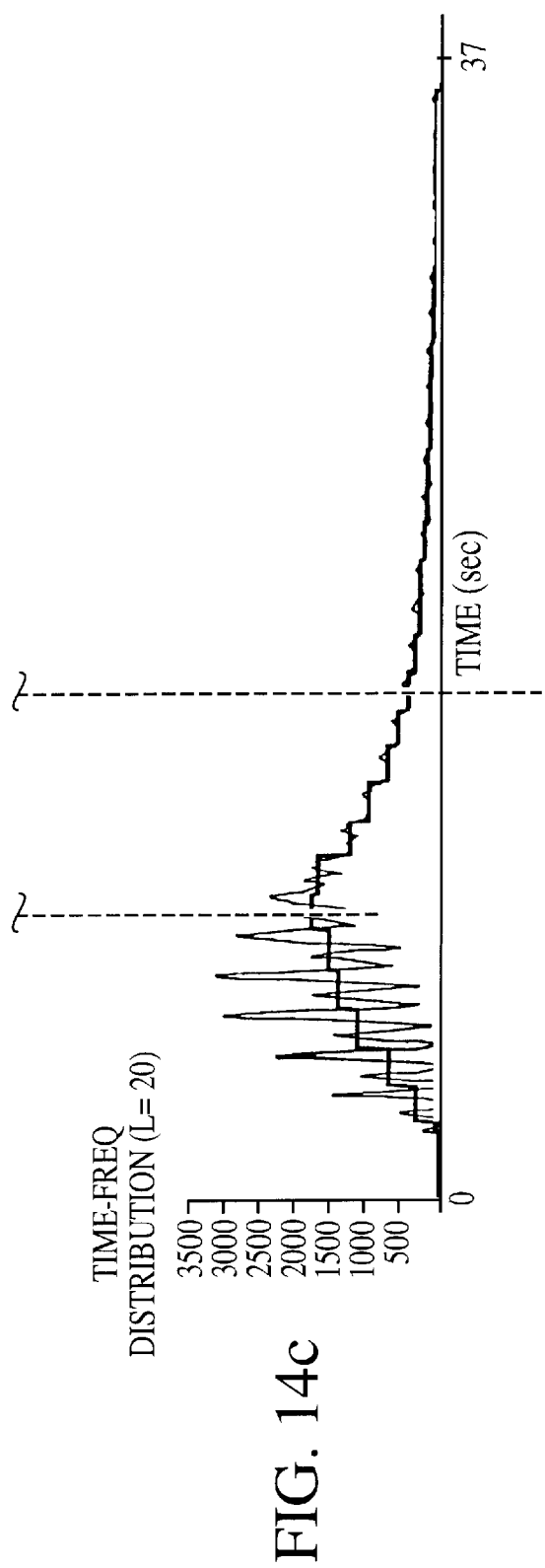
Figure 14D:
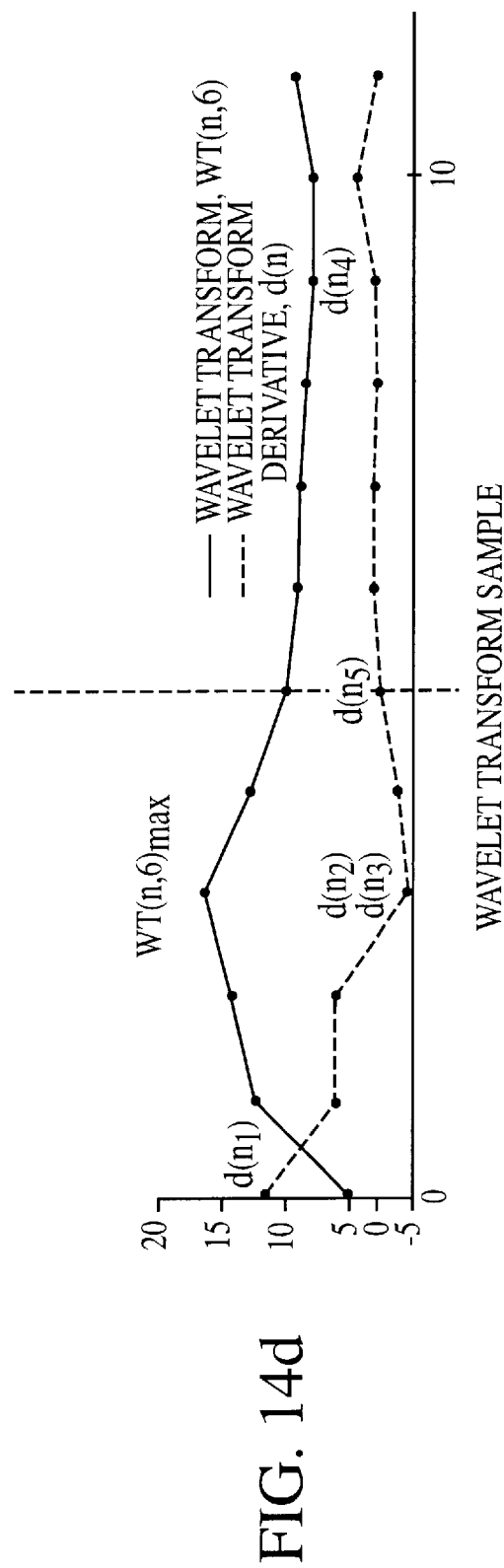

FIG. 14d illustrates the relationship of the wavelet transform WT(n,6) and derivative thereof, d(n), as related to the arterial pressure (FIG. 14a), blood velocity (FIG. 14b), and time frequency distribution (FIG. 14c).

While the embodiment illustrated in FIG. 16 and described above involves the application of a Haar wavelet transform, it will be recognized that other types of transforms and mathematical operations may be substituted consistent with the present invention to isolate the "settling point" associated with the end diastolic velocity; hence, the use of a Haar transform is merely illustrative.

Derivation of Scaling Factors

Based on the foregoing information, a first scaling factor, $F_1$, may be derived using the following equation:

$$F_1 = \frac{MAP(n') - MAP(n^*)}{MAP(n') - Diastole(n')}, \quad (11)$$

where n' is the sample identified by the time-frequency algorithm during which the measured MAP corresponds to the catheter MAP, and $n^*$ is the sample identified by the wavelet algorithm during which the measured MAP corresponds to the catheter diastole. For the waveforms associated with the zeroeth order model previously described (see Appendix B), $$F_1 = \frac{1}{b_0}.$$

In one embodiment, this scaling factor is only calculated intermittently during a calibration sweep.

While the catheter pressure is not changing significantly, the applanation may be fixed at a low, constant externally applied pressure. During this "steady state" condition, the measured MAP, $MAP_{SS}$, and measured diastolic pressure, $Diastole_{SS}$, will not change significantly. A second, "steady state" scaling factor, $F_2$, can therefore be derived using the following equation:

$$F_2 = \frac{MAP(n') - MAP(n^*)}{MAP_{ss} - Diastole_{ss}}. \tag{12}$$

FUZZY Logic Controller and MAP Servo

As previously discussed with respect to FIGS. 8 and 9 above, one embodiment of the invention includes one or more fuzzy logic controllers (circuits) 847, 849. The fuzzy logic controller employed in the applanation motor control circuit 847 is used to servo the MAP, and possesses two inputs and one output. The two input signals of this embodiment of the control circuit 847 are based on the time-frequency signal previously described herein. Other numbers and types of inputs may conceivably be used, however, as is well understood in the art.

To calculate this time-frequency signal, the blood velocity is first acquired at a first sampling frequency f1, thereby resulting in a digitized signal. In the illustrated embodiment, the blood velocity is sampled at a frequency of 400 Hz using a National Instruments ADC, Model No. DaQCard-AI-16E-4, resulting in digitized data with 12 bit resolution. It will be recognized, however, that other sampling frequencies, data conversion devices, and digital data resolution values may be substituted with equal success. The digitized data is then decimated by a factor of 20 to obtain 20 Hz data. The Pseudo-Wigner distribution at 0 Hz is calculated using Eqn. 4 above, with L=window length=5. The mean time-frequency signal is then calculated for each waveform.

The embodiment of the controller described herein seeks to maximize the mean time-frequency signal on a per-waveform (beat) basis, although other criteria may conceivably be used. The mean time-frequency signal is proportional to the end-diastolic blood velocity. The mean time-frequency signal for each waveform is passed to the fuzzy logic controller 847 as the first input. A second input to the controller 847 is derived as the difference between the current and last mean time-frequency inputs. The fuzzy logic controller 847 calculates the number of applanation steps to output as a multiple of 50 steps, ranging from −400 to +400 steps (38,400 nominal steps=1 inch). If the difference input is positive (+), the output signal directs the applanation motor to continue in the same direction for a calculated number of steps. If the difference input is negative (−), the output signal directs the applanation motor to change direction for a calculated number of steps. The input and output membership functions of the controller are typical functions of the type well known in the controller arts with 5 overlapping trapezoids, although it will be recognized that other types of membership functions may be used. Fuzzification of the illustrated embodiment uses the standard AND rule; defuzzification uses the standard centroid method.

The shift in end-diastolic velocity that is the basis of the mean time-frequency signal previously described has been anecdotally observed by the Applicant herein to be continuously present in anesthetized operating room subjects during two hour studies. Appendix C describes these observations in greater detail.

Scaling During MAP Servo

Figure 17:
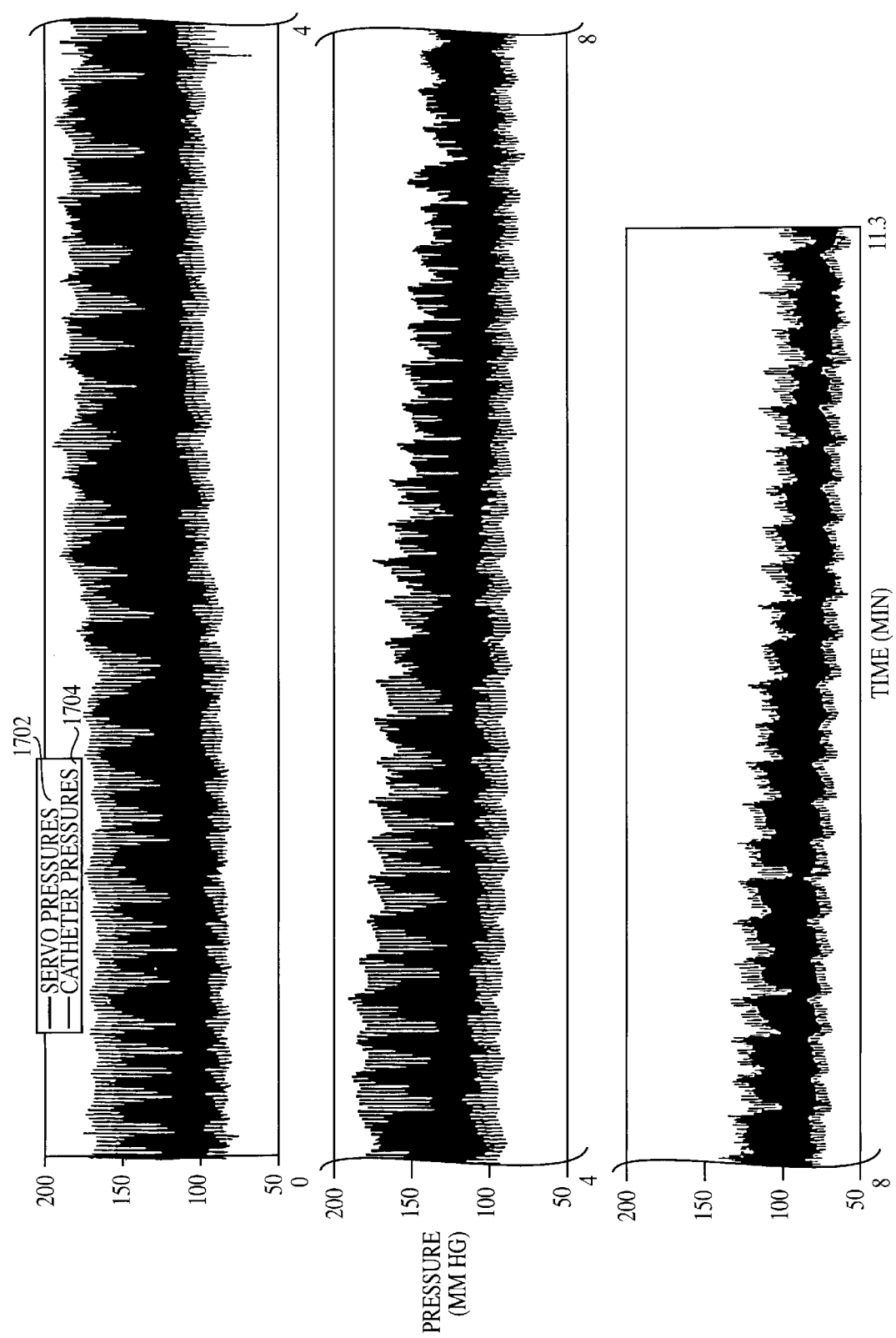
FIG. 17 is a graph illustrating the response of the servo algorithm of the invention to the time-variant arterial (catheter) blood pressure of a test subject.
Figure 18:
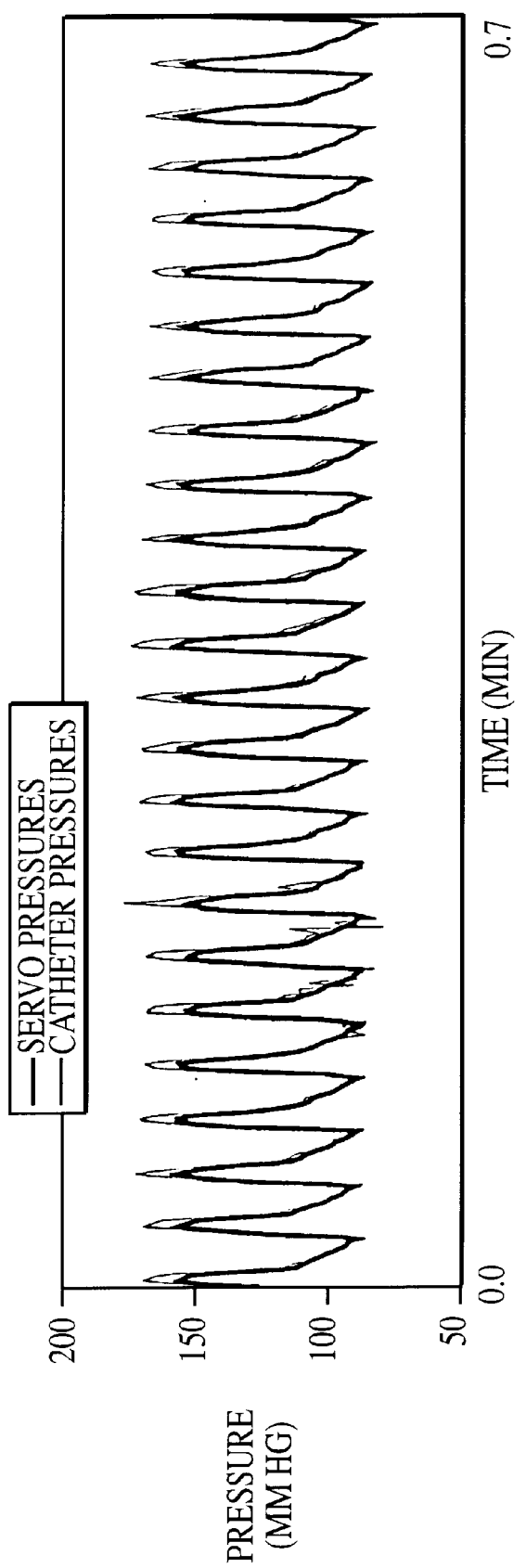
FIG. 18 is a graph illustrating three selected portions of the servo algorithm response of FIG. 17 in detail.
Figure 18:
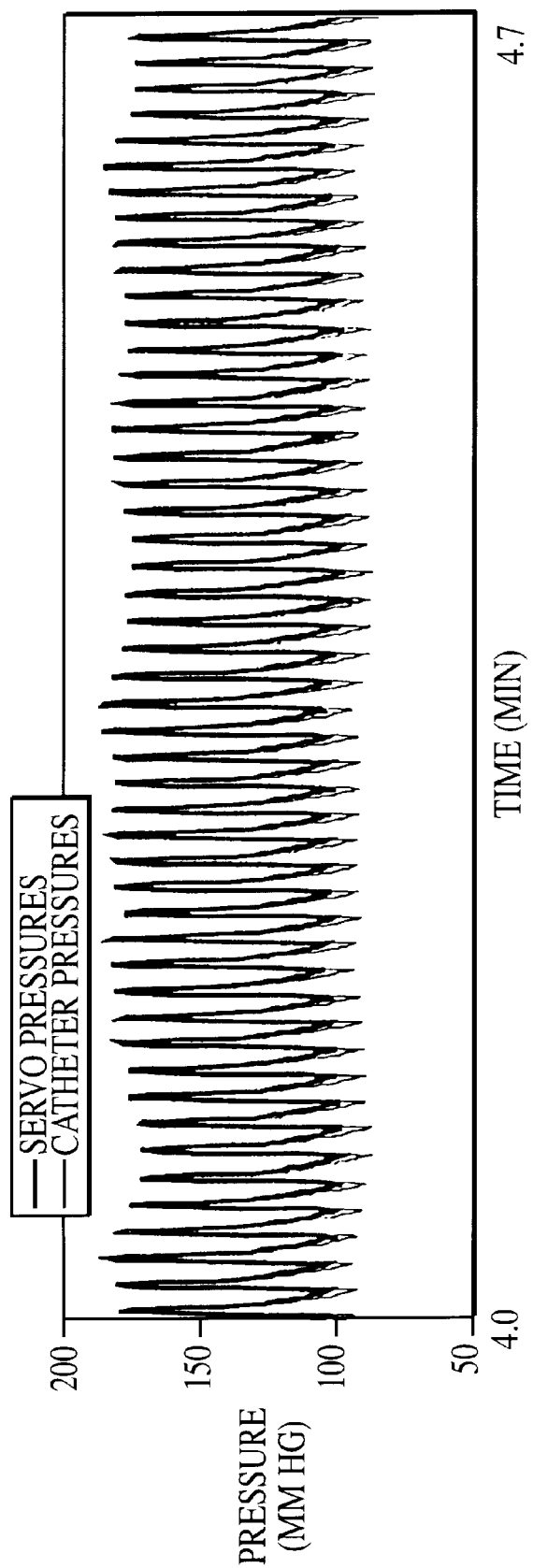
Figure 18:
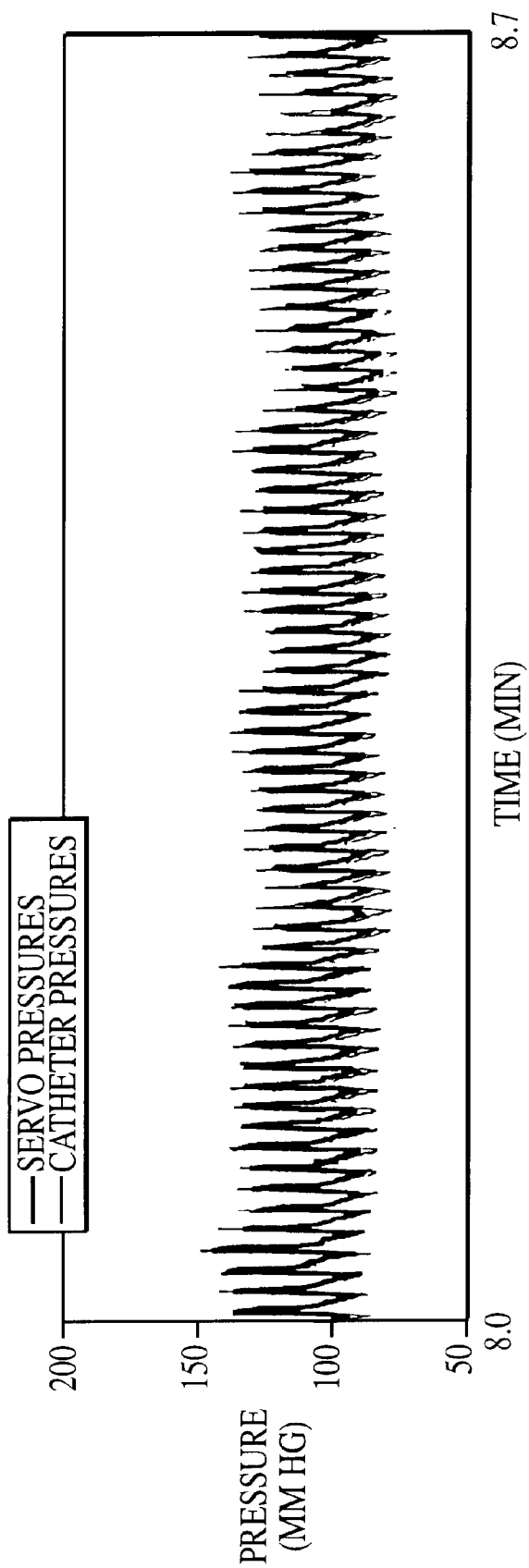
Figure 19:
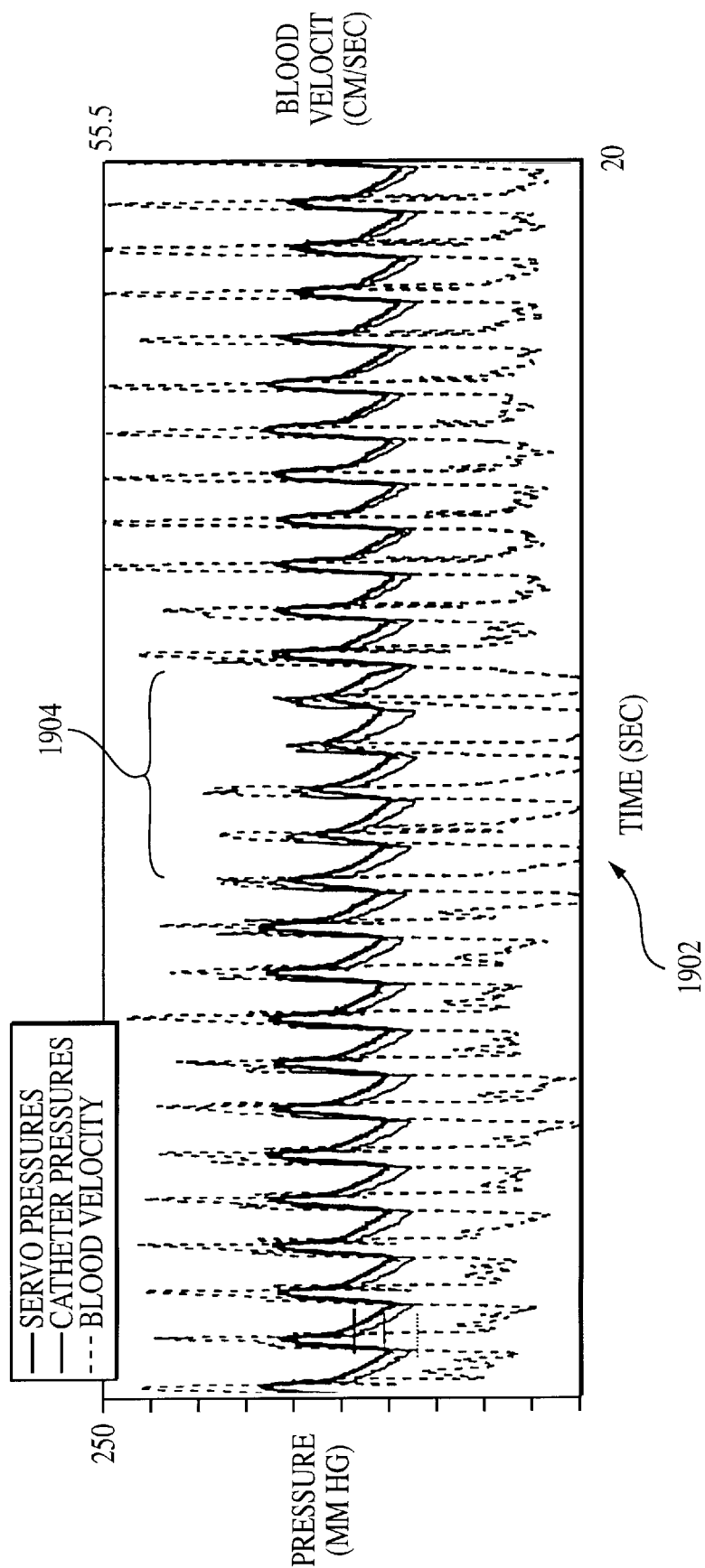
FIG. 19 is a graph illustrating a selected portion of the data presented in FIG. 17, demonstrating the self-correction response of the servo algorithm.

Between intermittent calibration sweeps, the applanation pressure is varied as previously described herein to continuously "servo" to the catheter MAP as the latter varies in time. A typical result obtained using the servo algorithm of the present invention is illustrated in FIGS. 17 through 19, and described in greater detail in Appendix C hereto. Referring to FIG. 17, the response of the algorithm to an observed 50 mm Hg drop in MAP over approximately 11 minutes for a single test subject (in response to epidural administration of the anesthetic bupivacaine) is illustrated. As shown in this Figure, the servo algorithm of the invention tracked the MAP accurately as shown by the overall correlation between servo pressure 1702 and catheter pressure 1704 over time. The mean error in tracking 552 pressure beats was 3±4 mm Hg. FIG. 18 is a detail view of FIG. 17, illustrating three forty (40) second windows of the catheter and servo data. FIG. 19 is a 20 second interval "snapshot" of the data of FIG. 17 that occurred at 6.5 minutes from onset of data recordation. As illustrated in FIG. 19, a significant drop 1902 in the end-diastolic velocity was corrected within 5 beats 1904.

By estimating the mean and diastolic pressures accurately using the foregoing method on an intermittent basis, the scaling factor, $F_1$, may be derived and applied for continuous estimation of systole and diastole, as well as the entire blood pressure waveform, $y_{scaled}(n)$:

$$y_{scaled}(n) = F_1(y_{servo}(n) - MAP_{servo}) + MAP_{servo}. \tag{13}$$

Scaling During Steady State Pressure

During periods of steady state pressures (i.e., when the catheter pressure does not vary significantly), a low constant applanation is applied externally to minimize trauma to the wrist of the subject. By estimating the catheter mean and diastolic pressures accurately, the scaling factor, $F_2$, may be derived and applied for continuous estimation of systole and diastole, as well as the entire blood pressure waveform:

$$y_{scaled}(n) = F_2(y_{ss}(n) - MAP_{ss}) + MAP(n'). \tag{14}$$

During continuous blood pressure estimation, the system will alternate between periods of servoing to the catheter MAP while blood pressure is in flux, and periods of applying a low constant applanation pressure while blood pressure is in steady state.

While the above detailed description has shown, described, and pointed out fundamental novel features of the invention as applied to various embodiments, it will be understood that various omissions, substitutions, and changes in the form and details of the apparatus and methods illustrated may be made by those skilled in the art without departing from the spirit of the invention.

APPENDIX A

Algorithm Experiments

To demonstrate the maximum time-frequency principle, 10 learning data files were selected from past applanation sweeps that possessed high quality ultrasound, overcompression, and generally large mean arterial pressure (MAP) difference. MAP difference was calculated by comparing estimated MAP to the average of two cuff MAPs measured immediately before and after an applanation sweep. Two additional files were acquired with an additional constraint of sweeping down to a minimum diastolic value less than 30 mm Hg below the true diastole (specifically files 11 and 12). The data files were acquired using a variety of sensor geometries, position angles (steel mount angles are varied and unknown), and subjects, as illustrated in Table 1.

TABLE 1

Learning Data

| File | Subject | Sensor | Sensor Position | Mean Cuff Avg. Pressure (mm hg) | Arterial Max Pulsatile Estimate (mm Hg) | Time-Frequency Estimate (mm Hg) |
|---|---|---|---|---|---|---|
| 1 | 1 | mo30 | steel mount | 108 | 122 | 103 |
| 2 | 2 | mo30 | steel mount | 88 | 90 | 82 |
| 3 | 3 | mo30 | steel mount | 68 | 85 | 84 |
| 4 | 4 | mo30 | steel mount | 88 | 83 | 83 |
| 5 | 4 | dc22 | 0° pitch, 0° roll | 85 | 90 | 86 |
| 6 | 5 | dc22 | −10° pitch, +10° roll | 63 | 51 | 58 |
| 7 | 2 | dc22 | −10° pitch, −10° roll | 84 | 90 | 92 |
| 8 | 6 | dc29 | 0° pitch, 0° roll | 77 | 104 | 105 |
| 9 | 7 | dc29 | +10° pitch, −10° roll | 88 | 107 | 81 |
| 10 | 8 | Mo30 | steel mount | 98 | 135 | 105 |
| 11 | 6 | Dc33 | 0° pitch, 0° roll | 82 | 124 | 87 |
| 12 | 3 | Dc19 | 0° pitch, 0° roll | 73 | 102 | 71 |
| | | | MAP error (mm Hg): | | 15 ± 17 | 3 ± 11 |

In each file, MAP was estimated by searching for the maximal pulsatile pressure. MAP as also estimated by determining the MAP associated with a pressure waveform with the maximal mean time-frequency distribution. The Pseudo Wigner distribution of the velocity, with k=0, calculated. Within each pressure waveform time interval, the mean distribution value was then calculated. The algorithm for calculating the maximal time-frequency distribution was "tuned" to the 12 files. By tuning, secondary algorithm steps such as the determination of the choice of the first pressure and velocity waveforms to be analyzed within a sweep were optimized. Also, the MAP differences using the maximum mean distribution versus maximum diastolic distribution were evaluated. While the results from both methods were insignificantly different, the maximum mean distribution was easier to calculate.

Once the mean time-frequency algorithm was tuned, the MAP in 6 new data files (again, with various sensor geometries, position angles, and subjects; see Table 2) was estimated and compared to the cuff MAP. For each comparison, the mean and standard deviation of the MAP difference was calculated. The paired, two-sided t test as used to assess significant differences between methods, using a 95% confidence interval.

TABLE 2

Testing Data

| File | Subject | Sensor | Sensor Position | Mean Cuff Avg. Pressure (mm Hg) | Arterial Max Pulsatile Estimate (mm Hg) | Time-Frequency Estimate (mm Hg) |
|---|---|---|---|---|---|---|
| 13 | 9 | Mo30 | steel mount | 73 | 93 | 73 |
| 14 | 4 | Dc18 | 0° pitch, 0° roll | 79 | 97 | 89 |
| 15 | 8 | Mo30 | steel mount | 88 | 114 | 95 |
| 16 | 2 | Mo30 | steel mount | 88 | 101 | 85 |
| 17 | 5 | Dc22 | +10° pitch, −10° roll | 64 | 60 | 64 |
| 18 | 2 | Dc33 | +10° pitch, −10° roll | 79 | 120 | 85 |
| | | | MAP error (mm Hg): | | 19 ± 15 | 3 ± 5 |

Results

For the learning data (Table 1), the maximum pulsatile MAP difference was 15±17 mm Hg; the maximum time-frequency MAP difference was 3±11 mm Hg. For the testing data (Table 2), the maximum pulsatile MAP difference was 19±15 mm Hg; the maximum time-frequency MAP difference was 3±5 mm Hg. In both the learning and testing data sets, the results obtained from the maximum time-frequency method were significantly different from those obtained using the maximum pulsatile method ($p \leq 0.02$ and $p \leq 0.03$, respectively).

APPENDIX B

Mechanical Impulse Response

In obtaining experimental verification of the methods disclosed herein, Applicant obtained data in 10 second intervals from three different human subjects in a hospital operating room. During these 10 second intervals, data was sampled at 400 Hz, and decimated to 100 Hz. The mean arterial pressures (MAPs) measured for each of the three subjects were 73, 126, and 83 mm Hg, respectively. These means were subtracted from the respective data sets for each subject, and fit to the ARX model using various combinations of N and M, as illustrated in Table B-1:

TABLE B-1

Combinations of Model Orders (N) and Number of Feedforward Coefficients (M)

| N | M |
|---|---|
| 4 | 3 |
| 10 | 9 |
| 2 | 1 |
| 1 | 1 |
| 0 | 1 |

For all three subjects, the optimum model was a zeroeth order model with one feedforward coefficient. The identified feedforward coefficients and their associated standards of deviation are shown in Table B-2.

TABLE B-2

Identified Feedforward Coefficients

| Subject | Mean (mm Hg) | $b_0$ | Standard Deviation |
|---------|--------------|-------|--------------------|
| 1 | 77 | 0.75 | 0.003 |
| 2 | 121 | 0.86 | 0.001 |
| 3 | 81 | 0.80 | 0.003 |

Estimate of Diastolic Pressure

Using the time-frequency algorithm for estimating catheter MAP (such as that described with respect to FIGS. 3a and 3b herein) in conjunction with the wavelet algorithm for estimating catheter diastolic pressure (FIG. 16 herein), pressures were estimated in 156 decreasing applanation sweeps experimentally obtained from 7 human subjects in a hospital operating room. The applanation sweeps were obtained during conditions having a variety of prevailing catheter MAP values, ranging from 48 to 132 mm Hg. A prototype ultrasound circuit having comparatively low sensitivity was used during these experiments. Estimated and catheter pressures were compared, with the mean error in MAP being 2±15 mm Hg, and the mean error in diastolic pressure being 5±14 mm Hg. The reported catheter pressure was averaged from the first, middle, and last waveforms obtained during a decreasing applanation sweep. Using one prior art tonometry approach of estimating the MAP when the peak-to-peak pressure was maximum (i.e., the maximum pulsatile method), the mean error in MAP was 11±20 mm Hg. The squared correlation coefficients, $r^2$, for these estimates were 0.67(p=0.030), 0.56(p=0.038), and 0.61(p=0.034), respectively.

APPENDIX C

When the ultrasonic/pressure sensor is positioned with respect to the subject's blood vessel to measure a pressure equivalent to the catheter mean, the end-diastolic velocity is maximized. In the controller example illustrated in FIGS. 17–19 herein, the catheter MAP dropped dramatically over 11 minutes. The maximum catheter MAP was 132 mm Hg; the minimum catheter MAP was 79 mm Hg. Over 552 beats, the mean error of the controller, compared to catheter MAP pressure, was 3±4 mm Hg. As shown in the 20 second snapshot that occurred at 6.5 minutes, (FIG. 19), a significant drop in the end-diastolic velocity was corrected within 5 beats.

Preliminary studies have been conducted by the Applicant herein to assess the accuracy of the fuzzy logic controller. Over a two hour period, two anesthetized operating room subjects were subjected to continuous two 20 minute intervals of measurement, followed by 5 minute intervals of rest. During each 20 minute measurement, an applanation pressure sweep was conducted, followed by continuous servo control. The catheter MAPs ranged from 69 to 106 mm Hg. Over 3,103 beats, the mean error of the controller MAPs, compared to catheter MAPs, was −3±5 mm Hg. Individual data sets are summarized in Table C-1 below.

TABLE C-1

Preliminary results of MAP servo control.
[Note: Following results are based on different subjects than the results used as the basis for FIGS. 17–19]

| Patient | Data Set | Pressure Range | # Beats | Error (mm Hg) |
|---------|----------|----------------|---------|---------------|
| 1 | 1 | 69–106 | 653 | −1 ± 5 |
| 1 | 2 | 82–93 | 830 | −6 ± 6 |
| 2 | 1 | 73–83 | 747 | −1 ± 4 |
| 2 | 2 | 81–93 | 873 | −4 ± 6 |

TOTAL: 3,103  MEAN: −3 ± 5

What is claimed is:

1. A method of continuously and non-invasively estimating the blood pressure existing within the artery of a subject, comprising:
   estimating the diastolic pressure within said artery;
   estimating the mean pressure within said artery;
   sensing a pressure waveform from said artery;
   deriving a scaling factor by modeling a mechanical impulse response of said artery as a mathematical function based at least in part on said estimated diastolic pressure and said estimated mean pressure; and
   continuously estimating the blood pressure within said artery based on said scaling factor, said sensed pressure waveform, and said mean pressure.

2. The method of claim 1, wherein said act of modeling a mathematical function comprises modeling as a linear autoregression function.

3. The method of claim 2, wherein said act of modeling as a linear autoregression function comprises selecting the order of said autoregression function based at least in part on standard deviation and residuals.

4. A method of continuously and non-invasively estimating the blood pressure existing within the artery of a subject, comprising:
   estimating the diastolic pressure within said artery;
   estimating the mean pressure within said artery by:
   (i) transmitting an acoustic signal into said artery;
   (ii) receiving an echo from said acoustic signal;
   (iii) analyzing said echo to estimate the velocity of said blood flowing in said artery;
   (iv) forming a time-frequency representation of said velocity; and
   (v) generating an estimate of mean blood pressure when said time-frequency representation satisfies a given condition;
   sensing a pressure waveform from said artery;
   deriving a scaling factor based at least in part on said estimated diastolic pressure and said estimated mean pressure; and
   continuously estimating the blood pressure within said artery based on said scaling factor, said sensed pressure waveform, and said mean pressure.

5. The method of claim 4, wherein said given condition comprises maximization of said time-frequency representation.

6. A method of continuously and non-invasively estimating the blood pressure existing within the artery of a subject, comprising:
   estimating a first pressure within said artery;
   estimating a second pressure within said artery;
   sensing a pressure waveform from said artery;
   deriving a scaling factor by modeling a mechanical impulse response of said artery as a linear autoregression function based at least in part on said estimated first and second pressures; and continuously estimating the blood pressure within said artery based on said scaling factor, said sensed pressure waveform, and said second pressure.

7. The method of claim 6, wherein said act of modeling as a linear autoregression function comprises selecting the order of said autoregression function based at least in part on standard deviation and residuals.

8. A method of continuously and non-invasively estimating the blood pressure existing within the artery of a subject, comprising:

estimating a first pressure within said artery;

estimating a second pressure within said artery, comprising:

transmitting an acoustic signal into and receiving an echo from said artery;

analyzing said echo to estimate the velocity of said blood flowing in said artery;

forming a time-frequency representation of said velocity; and generating an estimate of said second pressure when said time-frequency representation satisfies a given condition;

sensing a pressure waveform from said artery;

deriving a scaling factor based at least in part on said estimated first and second pressures; and continuously estimating the blood pressure within said artery based on said scaling factor, said sensed pressure waveform, and at least one of said first and second pressures.

9. The method of claim 8, wherein said given condition comprises maximization of said time-frequency representation.

10. Apparatus for continuously and non-invasively estimating the blood pressure existing within the artery of a subject, comprising:

a sensor adapted to detect a pressure waveform from said artery and generate electrical signals relating thereto;

a processor operatively coupled to said sensor and adapted to process said electrical signals, said processing of said signals comprising at least:

(i) estimating a first pressure within said artery;

(ii) estimating a second pressure within said artery;

(iii) deriving a scaling factor by modeling a mechanical impulse response of said artery as a function based at least in part on said estimated first and second pressures; and (iv) continuously estimating the blood pressure within said artery based on said scaling factor, said pressure waveform, and at least one of said first and second pressures.

11. Apparatus as defined in claim 10, wherein said act of modeling as a function comprises (i) modeling as a linear autoregression function; and (ii) selecting the order of said autoregression function based at least in part on standard deviation and residuals.

12. Apparatus with means for continuously and non-invasively estimating the blood pressure existing within the artery of a subject, comprising:

means for detecting a pressure waveform from said artery, including means for generating electrical signals relating thereto;

processor means operatively coupled to said means for detecting for processing said electrical signals, said processing of said signals comprising at least:

(i) estimating a first pressure within said artery;

(ii) estimating a second pressure within said artery;

(iii) deriving a scaling factor by modeling a mechanical impulse response of said artery as a mathematical function based at least in part on said estimated first and second pressures; and (iv) continuously estimating the blood pressure within said artery based on said scaling factor, said pressure waveform, and at least one of said first and second pressures.

13. Apparatus as defined in claim 12, wherein said act of modeling as a mathematical function comprises (i) modeling as a linear autoregression function, and (ii) selecting the order of said autoregression function based at least in part on standard deviation and residuals.

14. A method of continuously and non-invasively estimating the blood pressure existing within the artery of a subject, comprising the steps of:

estimating a first pressure within said artery;

estimating a second pressure within said artery;

sensing a pressure waveform from said artery;

modeling a mechanical impulse response of said artery as a mathematical function based at least in part on said estimated first and second pressures to derive a scaling factor; and using said scaling factor, said sensed pressure waveform, and said second pressure to estimate continuously the blood pressure within said artery.

15. The method of claim 14, wherein said act of modeling as a mathematical function comprises (i) modeling as a linear autoregression function and (ii) selecting the order of said autoregression function based at least in part on standard deviation and residuals.

* * * * *